(12) United States Patent
Sugaya et al.

(10) Patent No.: US 7,888,119 B2
(45) Date of Patent: Feb. 15, 2011

(54) TISSUE SUBSTITUTES COMPRISING STEM CELLS AND REDUCED CERIA

(75) Inventors: Kiminobu Sugaya, Winter Park, FL (US); Stephanie Merchant, Sanford, FL (US); Sudipta Seal, Oviedo, FL (US); Petya Georgieva, Williamsville, NY (US); Manny Vrotsos, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 77 days.

(21) Appl. No.: 11/582,057

(22) Filed: Oct. 16, 2006

(65) Prior Publication Data

US 2007/0123996 A1    May 31, 2007

Related U.S. Application Data

(60) Provisional application No. 60/727,075, filed on Oct. 14, 2005.

(51) Int. Cl.
 *C12N 5/00* (2006.01)
 *A01N 63/00* (2006.01)
 *A61K 51/00* (2006.01)
(52) U.S. Cl. ............... 435/395; 435/325; 424/93.1; 424/1.29

(58) Field of Classification Search ............ 435/395, 435/325; 424/93.1, 1.29
See application file for complete search history.

(56) References Cited

U.S. PATENT DOCUMENTS

| | | | |
|---|---|---|---|
| 7,141,227 B2 * | 11/2006 | Chan | 423/263 |
| 7,270,813 B2 * | 9/2007 | Shimp et al. | 424/93.7 |
| 2003/0050709 A1 | 3/2003 | Noth et al. | |
| 2003/0100948 A1 | 5/2003 | Goulet et al. | |
| 2005/0159820 A1 | 7/2005 | Yoshikawa et al. | |
| 2005/0164377 A1 | 7/2005 | Miyabayashi et al. | |

OTHER PUBLICATIONS

Ohgushi et al. J. Biomed. Mat. Res. 48:913-927; 1999.*
Maschio et al. J. Mat. Sci. 27:5591-5596; 1992.*
Ramsfjell et al. Blood 99:4093-41.2; 1999.*
Devasenpathi et al. Mat. Let. 57:882-886; 2002.*

* cited by examiner

*Primary Examiner*—Fereydoun G Sajjadi
(74) *Attorney, Agent, or Firm*—Timothy H. Van Dyke; Beusse Wolter Sanks Mora & Maire

(57) ABSTRACT

A biocompatible composite includes a solid biocompatible material and a plurality of living human progenitor or living stem cells attached thereto. The biocomposite provides a stable interface with endogenous tissue and the implanted composition resulting in accelerated repair to damaged bones and tissues.

14 Claims, 2 Drawing Sheets
(1 of 2 Drawing Sheet(s) Filed in Color)

TISSUE SUBSTITUTES COMPRISING STEM CELLS AND REDUCED CERIA

CROSS-REFERENCE TO RELATED APPLICATIONS

The present application claims the priority of U.S. provisional patent application Ser. No. 60/727,075 and entitled "STEM CELL COMPRISING TISSUE SUBSTITUTES" filed Oct. 14, 2005 which is herein incorporated by reference in its entirety.

STATEMENT REGARDING FEDERALLY SPONSORED RESEARCH OR DEVELOPMENT

The United States Government has certain rights in this invention pursuant to Office of Naval Research Young Investigator Award (ONR-YIP) grant no. ONR N000140210591, Defense University Research Instrumentation Program (DURIP) grant no. ONR N000140310858 and Neuroreplacement strategies by mesenchymal stem cell (1 R01 AG 23472-01) from NIH.

FIELD OF THE INVENTION

The invention relates to the field of tissue engineering, production of connective tissue, such as tissue linked to natural bones or synthetic bone substitutes.

DESCRIPTION OF RELATED ART

Researchers in the surgical arts have been working for many years to develop new techniques and materials for use as grafts to replace or repair damaged or torn tissue structures, particularly bones and connective tissues, such as ligaments and tendons, and to hasten soft tissue repair. It is very common today for an orthopedic surgeon to harvest a central portion of patellar tendon of autogenous or allogenous origin for use as a replacement for a torn cruciate ligament. The surgical methods for such approaches are well known. Further it has become common for surgeons to use implantable prostheses formed from plastic, metal and/or ceramic material for reconstruction or replacement of physiological structures. Yet despite their wide use, surgically implanted prostheses present many attendant risks to the patient. Surgeons are in need of a non-immunogenic, high tensile strength graft material which can be used for surgical repair of bones, tendons, ligaments and other functional tissue structures.

Composites including partially stabilized zirconia, bioactive glass or glass-ceramics polyethylene-hydroxyapatite have been disclosed for the repair, reconstruction and replacement of diseased or damaged parts of the body, including bone. However, a stable interface with connective tissue has prevented clinical use of such biomaterials.

SUMMARY

A biocomposite comprises biocompatible material having plurality of living human progenitor or living stem cells attached to a surface thereof. The human progenitor or living stem cells provides a stable interface with endogenous tissue (e.g. bone) that has before the invention prevented clinical use of such biomaterials.

In a preferred embodiment, the biocompatible material is a porous material. Preferably, the porous or non-porous biocompatible material comprises a rare earth stabilized zirconia. In a most preferred embodiment, the biocompatible material comprises cerium oxide (ceria) stabilized zirconia. Ceria preferably comprises at least about 10 weight % of the bicompatible material, and is preferably more than 15 wt %, such as 20 wt %.

In another preferred embodiment, a biocomposite, comprises a biocompatible solid material, and a plurality of living human progenitor or living stem cells attached to a surface of said biocompatible material. In one aspect the biocompatible material is a porous material. In another aspect, the biocompatible material is solid providing a surface framework for cells to adhere and reconstitute the damaged tissue or organ.

Ceria provides unique oxidation state transformations and when plasma processing described herein is utilized for formation including non-equilibrium tetragonal phase formation. In a preferred embodiment, the biocompatible material comprises a reduced state of ceria molecules on surfaces of said material. Preferably, the surface of the biocompatible material comprises from about 10% to about 99% $Ce^{3+}$ molecules versus $Ce^{4+}$ molecules. Preferably, the surface of the biocompatible material comprises at least about 10% $Ce^{3+}$ molecules versus $Ce^{4+}$ molecules; more preferably, the biocompatible material comprises about 20% $Ce^{3+}$ molecules versus $Ce^{4+}$ molecules; more preferably, the surface of the biocompatible material comprises about 30% $Ce^{3+}$ molecules versus $Ce^{4+}$ molecules.

In another preferred embodiment, the surface of the biocompatible material comprises from about 10% to about 99% $Ce^{4+}$ molecules versus $Ce^{3+}$ molecules.

In another preferred embodiment, a method of repairing bone, comprises the steps of: obtaining live stem cells from a patient to be treated or a haplotype matched donor; culturing said stem cells with a biocompatible solid material, wherein said stem cells attach to a surface of said biocompatible material to form a biocomposite, and, positioning said biocomposite in proximity to bone to be treated, wherein said live stem cell provides an interface between said biocompatible material and said bone, wherein said biocomposite accelerates healing of said bone.

In one embodiment, the biocompatible material is a porous material. In an alternative embodiment, the biocompatible material is solid material (little or no pores, or pores that are smaller than the size of a cell). Preferably, the biocompatible material comprises ceria stabilized zirconia. By modifying the process parameters, controlled porosity on the surface of the biocompatible material, acts as scaffolding.

In a preferred embodiment, the biocompatible material comprises a plurality of stem cell coated cores, further comprising the step of placing said plurality of coated cores inside of said bone.

In another preferred embodiment, the biocompatible material is cultured with stem cells derived from autologous bone marrow. The stems cells are preferably, $Lin^-$, or $Sca-1^+$, or $c-kit^+$, and/or $Lin^- Sca-1^+ c-kit^+$.

In another preferred embodiment, the stem cells are transduced with a vector expressing a desired molecule, such as growth factors, stem cell targeting antigens, and the like. Preferably, the expressed molecules, include, but are not limited to: bone morphogenic protein such as, OP-1, OP-2, OP-3, COP-1, COP-3, COP-4, COP-5, COP-7, COP-16, BMP-2, BMP-3, BMP-3b, MP-4, BMP-5, BMP-6, BMP-9, BMP-10, BMP-11, BMP-12, BMP-13, BMP-14, B-15, BMP-16, BMP-17, BMP-18, GDF-1, GDF-2, GDF-3, GDF-5, GDF-6, GDF-7, GDF-8, GDF-9, GDF-10, GDF-11, GDF-12, MP121, dorsalin-1, DPP, Vg-1, Vgr-1, 6 A protein, NODAL, UNIVIN, SCREW, ADMP, NEURAL, TGF-β and conservative amino acid sequence variants thereof having osteogenic activity. Other examples of useful molecules include, but are not limited to: SCG 10; Na Channel II; glut-2, synapsin, epo, SCF, shh, wint, BMPs Ephrins, Pax-6, Emx-2, Mash-1, jagged 1 and 2, notch- and 2, ephrin B2 and ephrin B4, Bmi-1, different homeobox genes HOXB4, Factor VIII, Factor IX, or mutant genes for β-glucocerebrosidase, erythropoietin ("EPO"), α-L-iduronidase, iduronate sulphatase, N-sulphatase, N-acetyl α-D-glucosaminidase, α-glucosamine-N-acetyltransferase, N-acetyl-α-D-glucosaminide-6-sulphatase, Galactosamine-6 sulphate sulphatase, β-galactosidase, N-acetyl-alactosamine-4-sulphatase, acid ceraminidase, acid sphingomyelinase, galactocerebroside β-galactosidase, arylsuphatase A, adenosine deaminase, α-L-fucosidase growth factors such as the interleukin family, angiogenesis stimulating or inhibiting factors such as the nitric oxide synthases (NOS1-3), vascular endothelial growth factors ("VEGF"), Angiostatin 1-7. Other examples of genes useful for introduction into isolated stem cells include those that encode von Willebrand factor, insulin, tissue plasminogen activator, any of the interleukins, or a growth factor. Some examples of interleukins include IL-1, -2, -3, -4, -5, -6, -7, -8, -9, -10, -11, -12, -13, -14, -15, -16, -17, -18, -19, -20, and -21. Some examples of suitable growth factors include erythropoietin, thrombopoietin, PDGF, G-CSF, GM-CSF, IGF, TGFβ, VEGF, LIF, CNTF, FGF, EGF and BMP (bone morphogenic protein).

In yet another embodiment of the invention, a method of repairing bone comprises the steps of obtaining live stem cells from a patient to be treated or a haplotype matched donor, culturing the stem cells with a biocompatible material, wherein the stem cells attach to a surface of the biocompatible material to form a biocomposite, and positioning the biocomposite in proximity to bone to be treated, wherein the stem cell provides an interface between the biocompatible material and the bone and differentiate to accelerate healing of the bone. The biocompatible material has been found to facilitate attachment of stem cells to surfaces of the material.

In another preferred embodiment, the biocompatible material is coated or treated with cell adhesion molecules. Examples of cell adhesive proteins, protein fragments, or peptides, include, but not limited to fibronectin, laminin, collagen, vitronectin, osteopontin, RGD peptides, RGDS peptides, YIGSR peptides, ICAM-1, PECAM-1, LFA-3, LFA-1, VLA-4, VLA-5, L-Selectin and HCAM. Bone tissue-specific collagen (e.g., Type I collagen) derived from a number of sources are also suitable, including soluble collagen, acid-soluble collagen, collagen soluble in neutral or basic aqueous solutions, as well as those collagens which are commercially available. In addition, Type II collagen, as found in cartilage, also may be used in combination with Type I collagen.

The present invention therefore provides therapeutic, structural, or cosmetic implants comprising the biocompatible material and at least one cell. Preferably, the at least one cell is a bone-forming or bone-degrading cell. Particularly useful cell types include chondrocytes, osteocytes, osteoblasts, osteoclasts, mesenchymal stem cells, fibroblasts, muscle cells, hepatocytes, parenchymal cells, cells of intestinal origin, nerve cells, and skin cells, and may be provided as primary tissue explants, preparations of primary tissue explants, isolated cells, cell lines, transformed cell lines, and host cells. The implants may also comprise additional components such as biologically active agents or factors that alter the characteristics (such as resorbability, strength, adherence, injectability, frictional characteristics, etc.).

The invention also provides methods of preparing such implants; methods of growing bone or cartilage in vivo or in vitro, at natural sites or ectopic sites; methods of osseous augmentation; and methods of diagnosing disease states by assaying tissue-forming potential of cells isolated from a host. Other aspects of the invention are described infra.

BRIEF DESCRIPTION OF THE DRAWINGS

The patent or application file contains at least one drawing executed in color. Copies of this patent or patent application in publication with the color drawing(s) will be provided by the Office upon request and payment of the necessary fee. The invention is pointed out with particularity in the appended claims. The above and further advantages of this invention may be better understood by referring to the following description taken in conjunction with the accompanying drawings, in which:

DETAILED DESCRIPTION

Figure 1:
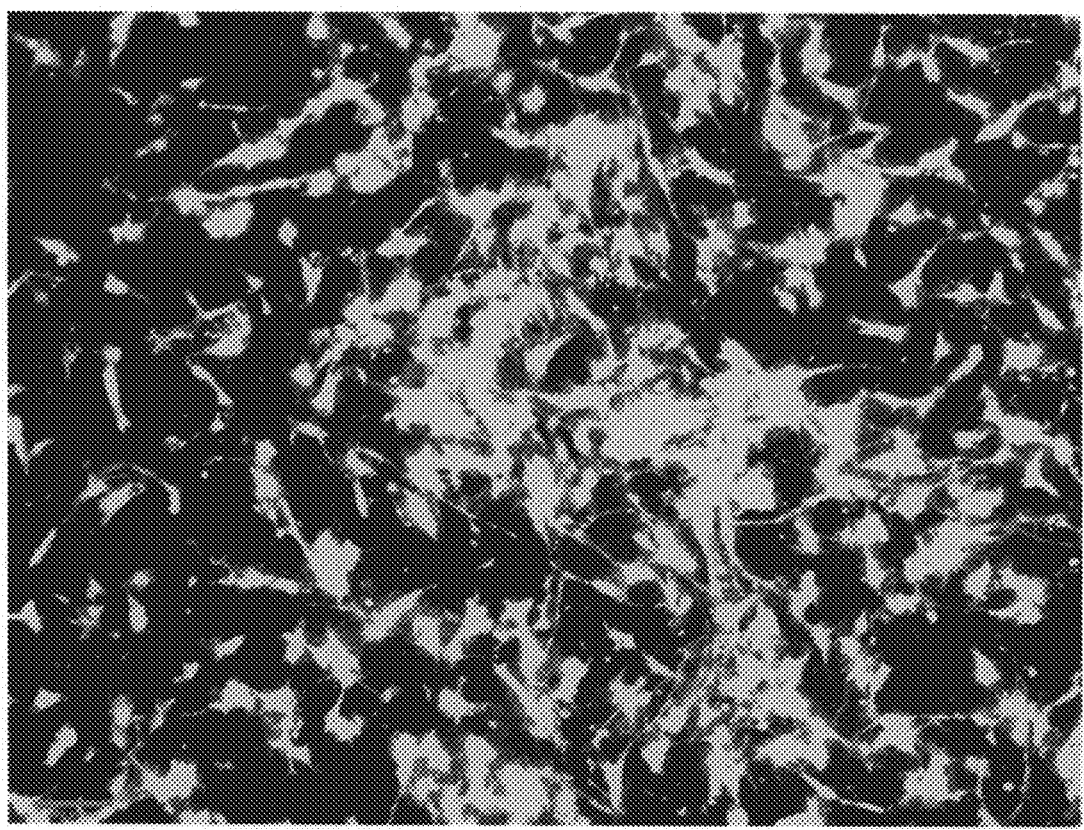
FIG. 1 shows a scanned image of mesenchymal stem cells isolated from adult human bone marrow cultured on synthetic bone according to the invention after staining with green fluorescent dye.

A biocomposite comprises a biocompatible solid material, and a plurality of living human progenitor or living stem cells attached to a surface of the biocompatible material. The stem cells on the surface of the biocomposite provides a stable interface with connective tissue which has been an unsolved issue for clinical use of biomaterials. The biocompatible material can be a macroscale article, or comprise a plurality of microscale or nanoscale core particles. The biocompatible material is preferably a porous material.

DEFINITIONS

The present section provides definitions of the terms used in the present invention in order to facilitate a better understanding of the invention.

As used herein, the singular forms "a", "an" and "the" include plural referents unless the context clearly dictates otherwise.

A "stem cell" is a relatively undifferentiated cell that can be induced to proliferate and that can produce progeny that subsequently differentiate into one or more mature cell types, while also retaining one or more cells with parental developmental potential. In many biological instances, stem cells are also "multipotent" because they can produce progeny of more than one distinct cell type, but this is not required for "stemness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype.

"Progenitor cells" have a cellular phenotype that is more primitive (i.e., is at an earlier step along a developmental pathway or progression than is a fully differentiated cell). Often, progenitor cells also have significant or very high proliferative potential. Progenitor cells may give rise to multiple distinct differentiated cell types or to a single differentiated cell type, depending on the developmental pathway and on the environment in which the cells develop and differentiate. Like stem cells, it is possible that cells that begin as progenitor cells might proceed toward a differentiated phenotype, but then "reverse" and re-express the progenitor cell phenotype.

"Differentiation" refers to the developmental process whereby cells assume a specialized phenotype, i.e., acquire one or more characteristics or functions distinct from other cell types. In most uses, the differentiated phenotype refers to a cell phenotype that is at the mature endpoint in some developmental pathway. In many but not all tissues, the process of differentiation is coupled with exit from the cell cycle—in these cases, the cells lose or greatly restrict their capacity to proliferate when they differentiate.

"Osteoinduction" refers to stimulating bone growth at a site within a subject at which little or no bone growth would occur if the site were left untreated. Sites which could therapeutically benefit from the induction of bone growth are referred to as "in need of osteoinduction". Examples include non-union fractures or other severe or massive bone trauma. It is noted that bone growth normally occurs at bone injuries such as simple or hairline fractures and well opposed complex fractures with minimal gaps without the need for further treatment. Such injuries are not considered to be "in need of osteoinduction". Simple fracture repair appears to be quite different from the induction of bone formation required to fill non-union fractures, segmental gaps or bone voids caused, for example, by removal of a bone tumor or cyst. These cases require bone grafting or induction of new bone growth generally employing some type of matrix or scaffolding to serve as a bone growth substitute. Induced bone growth can also be therapeutically beneficial at certain sites within a subject (referred to as "ectopic" sites) where bone tissue would not normally be found, such as a site in need of a bone graft or bone fusion. Fusions are commonly used to treat lower back pain by physically coupling one or more vertebrae to its neighbor. The bone created by such a fusion is located at a site not normally occupied by bone tissue. Osteoinduction at these ectopic sites can act as a "graft substitute" whereby induced bone growth between the vertebrae takes the place of a graft and obviates the need for a second operation to harvest bone for the grafting procedure. Induction of bone growth is also needed for treating acquired and congenital craniofacial and other skeletal or dental anomalies (see e.g., Glowacki et al., Lancet 1: 959 (1981)); performing dental and periodontal reconstructions where lost bone replacement or bone augmentation is required such as in a jaw bone; and supplementing alveolar bone loss resulting from periodontal disease to delay or prevent tooth loss (see e.g., Sigurdsson et al., J. Periodontol., 66: 511 (1995)).

"Amorphous"—By "amorphous" as that term is used here, it is meant a material with significant amorphous character. Significant amorphous character contemplates greater than 75% amorphous content, preferably greater than 90% amorphous content, and is characterized by a broad, featureless X-ray diffraction pattern. It is recognized that a small degree of crystallinity may exist in such material.

"Bioactive"—"Bioactive" refers to a material that induces hard tissue formation in and about the implant. When implanted in soft tissue, the bioactivity may also require the presence of a growth or trophic factor, or the seeding of the implant with a hard tissue forming cell type.

"Biocompatible"—The term "biocompatible", as used herein, means that the material does not elicit a substantial detrimental response in the host. There is always concern, when a foreign object is introduced into a living body, that the object will induce an immune reaction, such as an inflammatory response that will have negative effects on the host. For example, although hydroxyapatite is generally considered to be "biocompatible", significant inflammation and tissue necrosis have been observed when crystalline hydroxyapatite microcarriers are inserted intramuscularly in animals (see, for example, IJntema et al., Int. J. Pharm 112:215, 1994).

"Bioresorbable"—"Bioresorbable" or "resorbable" refers to the ability of a material to be resorbed in vivo. "Full" resorption means that no significant extracellular fragments remain. The resorption process involves elimination of the original implant materials through the action of body fluids, enzymes or cells. Resorbed calcium phosphate may, for example, be redeposited as bone mineral, or by being otherwise reutilized within the body, or excreted. "Strongly bioresorbable", as that term is used herein, means that at least 80% of the total mass of material implanted intramuscularly or subcutaneously is resorbed within one year.

"Cells"—the term "cells", as used herein, refers to any preparation of living tissue, including primary tissue explants and preparations thereof, isolated cells, cells lines (including transformed cells), and host cells.

"Effective Amount"—An effective amount of a biologically active agent is an amount sufficient to elicit a desired biological response.

"Biodegradable agent" refers to a resorbable biocompatible material such as a material that degrades gradually at the implant site. The material is capable of encapsulating a bioactive agent to provide time release or sustained release delivery of the bioactive agent. The biodegradable material encompasses natural and synthetic polymers. Examples of biodegradable material are poly(L-lactide) (PLLA), poly(D, L-lactide) (PDLLA), polyglycolide (PGA), poly(lactide-co-glycolide) (PLGA) and co-polymers thereof.

"Bone" refers to a calcified (mineralized) connective tissue primarily comprising a composite of deposited calcium and phosphate in the form of hydroxyapatite, collagen (primarily Type I collagen) and bone cells such as osteoblasts, osteocytes and osteoclasts, as well as to bone marrow tissue which forms in the interior of true endochondral bone. Bone tissue differs significantly from other tissues, including cartilage tissue. Specifically, bone tissue is vascularized tissue composed of cells and a biphasic medium comprising a mineralized, inorganic component (primarily hydroxyapatite crystals) and an organic component (primarily of Type I collagen). Glycosaminoglycans constitute less than 2% of this organic component and less than 1% of the biphasic medium itself, or of bone tissue per se. Moreover, relative to cartilage tissue, the collagen present in bone tissue exists in a highly-organized parallel arrangement. Bony defects, whether from degenerative, traumatic or cancerous etiologies, pose a formidable challenge to the reconstructive surgeon. Particularly difficult is reconstruction or repair of skeletal parts that comprise part of a multi-tissue complex, such as occurs in mammalian joints.

"Bone formation" means formation of endochondral bone or formation of intramembranous bone. In humans, bone formation begins during the first 6-8 weeks of fetal development. Progenitor stem cells of mesenchymal origin migrate to predetermined sites, where they either: (a) condense, proliferate, and differentiate into bone-forming cells (osteoblasts), a process observed in the skull and referred to as "intramembranous bone formation" or, (b) condense, proliferate and differentiate into cartilage-forming cells (chondroblasts) as intermediates, which are subsequently replaced with bone-forming cells. More specifically, mesenchymal stem cells differentiate into chondrocytes. The chondrocytes then become calcified, undergo hypertrophy and are replaced by newly formed bone made by differentiated osteoblasts, which now are present at the site. Subsequently, the mineralized bone is extensively remodeled, thereafter becoming occupied by an ossicle filled with functional bone-marrow elements. This process is observed in long bones and referred to as "endochondral bone formation." In postfetal life, bone has the capacity to repair itself upon injury by mimicking the cellular process of embryonic endochondral bone development. That is, mesenchymal progenitor stem cells from the bone-marrow, periosteum, and muscle can be induced to migrate to the defect site and begin the cascade of events described above. There, they accumulate, proliferate, and differentiate into cartilage, which is subsequently replaced with newly formed bone.

"Bone morphogenic protein (BMP)" refers to a protein belonging to the BMP family of the TGF-β superfamily of proteins (BMP family) based on DNA and amino acid sequence homology. A protein belongs to the BMP family according to this invention when it has at least 50% amino acid sequence identity with at least one known BMP family member within the conserved C-terminal cysteine-rich domain which characterizes the BMP protein family. Members of the BMP family may have less than 50% DNA or amino acid sequence identity overall.

"Conservative substitutions" are residues that are physically or functionally similar to the corresponding reference residues. That is, a conservative substitution and its reference residue have similar size, shape, electric charge, chemical properties including the ability to form covalent or hydrogen bonds, or the like. Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine. The term "conservative variant" or "conservative variation" also includes the use of a substituting amino acid residue in place of an amino acid residue in a given parent amino acid sequence, where antibodies specific for the parent sequence are also specific for, i.e., "cross-react" or "immunoreact" with, the resulting substituted polypeptide sequence.

"Defect" or "defect site" refers to a site requiring bone, joint, cartilage or ligament repair, construction, fusion, regeneration or augmentation. The site may be an orthopedic structural disruption or abnormality, or a site where bone does not normally grow. The defect further can define an osteochondral defect, including a structural disruption of both the bone and overlying cartilage. A defect can assume the configuration of a "void", which is understood to mean a three-dimensional defect such as, for example, a gap, cavity, hole or other substantial disruption in the structural integrity of a bone or joint. A defect can be the result of accident, disease, surgical manipulation, and/or prosthetic failure. In certain embodiments, the defect is a void having a volume incapable of endogenous or spontaneous repair. Such defects in long bone are generally twice the diameter of the subject bone and are also called "critical size" defects. For example, in a canine ulna defect model, the art recognizes such defects to be approximately 3-4 cm. Generally, critical size defects are approximately 1.0 cm, and incapable of spontaneous repair. See, for example, Schmitz et al., *Clinical Orthopaedics and Related Research*, 205, pp. 299-308 (1986); and Vukicevic et al., in *Advances in Molecular and Cell Biology*, 6, pp. 207-224 (1993)(JAI Press, Inc.). In rabbit and monkey segmental defect models, the gap is approximately 1.5 cm and 2.0 cm, respectively. In other embodiments, the defect is a non-critical size segmental defect. Generally, these are capable of spontaneous repair. In certain other embodiments, the defect is an osteochondral defect, such as an osteochondral plug. Such a defect traverses the entirety of the overlying cartilage and enters, at least in part, the underlying bony structure. In contrast, a chondral or subchondral defect traverses the overlying cartilage, in part or in whole, respectively, but does not involve the underlying bone. Other defects susceptible to repair using the instant invention include, but are not limited to, non-union fractures; bone cavities; tumor resection; fresh fractures (distracted or undistracted); cranial, maxillofacial and facial abnormalities, for example, in facial skeletal reconstruction, specifically, orbital floor reconstruction, augmentation of the alveolar ridge or sinus, periodontal defects and tooth extraction socket; cranioplasty, genioplasty, chin augmentation, palate reconstruction, and other large bony reconstructions; vertebroplasty, interbody fusions in the cervical, thoracic and lumbar spine and posteriolateral fusions in the thoracic and lumbar spine; in osteomyelitis for bone regeneration; appendicular fusion, ankle fusion, total hip, knee and joint fusions or arthroplasty; correcting tendon and/or ligamentous tissue defects such as, for example, the anterior, posterior, lateral and medial ligaments of the knee, the patella and achilles tendons, and the like as well as those defects resulting from diseases such as cancer, arthritis, including osteoarthritis, and other bone degenerative disorders such as osteochondritis dessicans.

"Morphogenic protein" refers to a protein having morphogenic activity (see below). Preferably a morphogenic protein of this invention comprises at least one polypeptide belonging to the BMP protein family. Morphogenic proteins may be capable of inducing progenitor cells to proliferate and/or to initiate differentiation pathways that lead to cartilage, bone, tendon, ligament, neural or other types of tissue formation depending on local environmental cues, and thus morphogenic proteins may behave differently in different surroundings. For example, an osteogenic protein may induce bone tissue at one treatment site and neural tissue at a different treatment site.

"Morphogenic protein stimulatory factor (MPSF)" refers to a factor that is capable of stimulating the ability of a morphogenic protein to induce tissue formation from a progenitor cell. The MPSF may have a direct or indirect effect on enhancing morphogenic protein inducing activity. For example, the MPSF may increase the bioactivity of another MPSF. Agents that increase MPSF bioactivity include, for example, those that increase the synthesis, half-life, reactivity with other biomolecules such as binding proteins and receptors, or the bioavailability of the MPSF.

"Osteogenic protein (OP)" refers to a morphogenic protein that is capable of inducing a progenitor cell to form cartilage and/or bone. The bone may be intramembranous bone or endochondral bone. Most osteogenic proteins are members of the BMP protein family and are thus also BMPs. As described elsewhere herein, the class of proteins is typified by human osteogenic protein (hOP-1). Other osteogenic proteins useful in the practice of the invention include osteogenically active forms of OP-1, OP-2, OP-3, BMP-2, BMP-3, BMP-4, BMP-5, BMP-6, BMP-9, DPP, Vgl, Vgr, 60A protein, GDF-1, GDF-3, GDF-5, GDF-6, GDF-7, BMP-10, BMP-11, BMP-13, BMP-15, UNIVIN, NODAL, SCREW, ADMP or NEURAL and amino acid sequence variants thereof. In one currently preferred embodiment, osteogenic protein includes any one of: OP-1, OP-2, OP-3, BMP-2, BMP-4, BMP-5, BMP-6, BMP-9, and amino acid sequence variants and homologs thereof, including species homologs thereof. Particularly preferred osteogenic proteins are those comprising an amino acid sequence having at least 70% homology with the C-terminal 102-106 amino acids, defining the conserved seven cysteine domain, of human OP-1, BMP-2, and related proteins. Certain preferred embodiments of the instant invention comprise the osteogenic protein, OP-1. As further described elsewhere herein, the osteogenic proteins suitable for use with applicants' invention can be identified by means of routine experimentation using the art-recognized bioassay described by Reddi and Sampath (Sampath et al., *Proc. Natl. Acad. Sci.*, 84, pp. 7109-13, incorporated herein by reference).

Proteins useful in this invention include eukaryotic proteins identified as osteogenic proteins (see U.S. Pat. No. 5,011,691, incorporated herein by reference), such as the OP-1, OP-2, OP-3 and CBMP-2 proteins, as well as amino acid sequence-related proteins, such as DPP (from *Drosophila*), Vgl (from *Xenopus*), Vgr-1 (from mouse), GDF-1 (from humans, see Lee, PNAS, 88, pp. 4250-4254 (1991)), 60A (from *Drosophila*, see Wharton et al. *PNAS*, 88, pp. 9214-9218 (1991)), dorsalin-1 (from chick, see Basler et al. *Cell* 73, pp. 687-702 (1993) and GenBank accession number L12032) and GDF-5 (from mouse, see Storm et al. *Nature*, 368, pp. 639-643 (1994)). The teachings of the above references are incorporated herein by reference. BMP-3 is also preferred. Additional useful proteins include biosynthetic morphogenic constructs disclosed in U.S. Pat. No. 5,011,691, incorporated herein by reference, e.g., COP-1, COP-3, COP-4, COP-5, COP-7 and COP-16, as well as other proteins known in the art. Still other proteins include osteogenically active forms of BMP-3b (see Takao, et al. *Biochem. Biophys. Res. Comm.*, 219, pp. 656-662 (1996)). BMP-9 (see WO95/33830), BMP-15 (see WO96/35710), BMP-12 (see WO95/16035), CDMP-1 (see WO 94/12814), CDMP-2 (see WO94/12814), BMP-10 (see WO94/26893), GDF-1 (see WO92/00382), GDF-10 (see WO95/10539), GDF-3 (see WO94/15965) and GDF-7 (see WO95/01802). The teachings of the above references are incorporated herein by reference. Some examples of suitable growth factors include erythropoietin, thrombopoietin, PDGF, G-CSF, GM-CSF, IGF, TGFβ, VEGF, LIF, CNTF, FGF, EGF and BMP (bone morphogenic protein).

"Repair" is intended to mean new bone and/or cartilage formation which is sufficient to at least partially fill the void or structural discontinuity at the defect. Repair does not, however, mean, or otherwise necessitate, a process of complete healing or a treatment which is 100% effective at restoring a defect to its pre-defect physiological/structural/mechanical state.

"Synergistic interaction" refers to an interaction in which the combined effect of two or more agents is greater than the algebraic sum of their individual effects.

Biocompatible Material

The invention provides the ability to coat the biomaterial surface with attached living stem cells isolated from adult tissue, bone marrow. Since stem cells are capable of differentiating into variety of cells according to the environmental cues, this technology provides both the interface between the biomaterial and host tissue, but also provides acceleration in the heeling of the wound. Furthermore, there is no ethical or immunorejection issues, which associate with fetal or embryonic stem cell technologies, because the source of the cells is the patient's tissue, or an immunological matched cells.

In a preferred embodiment, the biocompatible material comprises a rare earth stabilized zirconia, preferably being ceria stabilized. The biocompatible material can be porous or non-porous and may be fashioned into a desired shape. For example, the material can be in the form of a structurally stable, three dimensional implant. The structurally stable, three dimensional implant can be, for example, a cube, cylinder, block or an appropriate anatomical form.

In preferred embodiments, the average pore size of the biocompatible material is in the range of 20-500 µm. In a preferred embodiment, the pore size is 20-190 µm. In another embodiment, the pore size is in the range of 20-95 µm. These pores provide residence spaces for the culturing of stem cells and for any infiltrating osteolytic cells and osteoblasts when the biocompatible material is embedded in the living body. In one embodiment, the pores are spherical and uniformly distributed. Spherical pores having an average diameter in the range of 20-500 µm are appropriate for osteoblast infiltration. Spherical pores also provide the porous body with the necessary mechanical strength during the period that new bone is being synthesized, thus preventing the bone from fracturing during this period. Since stem cells are capable of differentiating into variety of cells according to the environmental cues, this technology provides not only the interface between the biomaterial and host tissue, but also accelerates the healing of the wound. Furthermore, there is no ethical or immunorejection issue, which associate with fetal or embryonic stem cell technologies, because the source of the cells is the patient tissue. Since stem cells provide an interface between the host and biomaterial, the invention can be applied to virtually any kind of tissue replacement.

As known by those having ordinary skill in the art, chemically, most of the rare earth (RE) elements (atomic numbers 57 through 71) are trivalent. Cerium alone is known to form compounds with a valence of +4, such as $CeO_2$ (ceria). Cerium is believed to be a unique material with regard to the mixed valence states provided, both +3 and +4. However, at least with regard to cerium oxide compounds, the vast majority of valence states are +4 states.

Cerium of valence +3 is generally referred to as cerous, while with valence +4 is generally referred to as ceric. Cerium oxide includes both ceric oxide and cerous oxide. Cerous oxide is also known as Cerium III oxide and has the formula $Ce_2O_3$. Ceric oxide is known as ceria, cerium dioxide and cerium IV oxide and has the chemical formula $CeO_2$.

The cerium oxide nanoparticles used with the invention have an average particle size <20 nm, preferably in the range from 1 to 10 nanometers, such as 3 to 7 nm. The inventors have found that an average cerium oxide nanoparticle size in the range <20 nm provides an unexpected and highly beneficial result which is believed to be based on an increased percentage of +3 valence states (relative to the generally more numerous +4 states) on the cerium oxide nanoparticles surface. The increasing percentage of +3 valence states is believed to increase as the cerium oxide nanoparticle size decreases in this size range. Surprisingly, the inventors have found that ceria ions in a reduced stated has lead to unexpected and surprising results with respect to cell attachment and growth. The reduced state of ceria molecules provides excellent results with respect to the growth of cells. Growth of cells increases with the reduced surface state of ceria.

The thickness range for the cerium oxide nanoparticles layer is preferably 100 to 300 nm, but can be thicker or thinner than this range, such as 20 nm to 1 µm. The cerium oxide nanoparticle layer is also preferably porous. The surfactant used in the reverse micelle process described below helps keeps the cerium oxide nanoparticles separate to provide a porous layer. The cerium oxide nanoparticles can be doped using trivalent elements, such as rare earth elements, such as La and Nd, which may increase the concentration of vacancies. The concentration range for trivalent doping elements is generally up to about 40 wt %.

Ceria nanoparticles are presently available commercially in the average size range from about 7 to 20 nm. However, such particles are formed from a high temperature process which renders the ceria nanoparticles highly agglomerated. For use with the invention, cerium oxide nanoparticles particles are preferably obtained in a non-agglomerated state. A reverse-micelle process using unique reagents can be used to form substantially non-agglomerated cerium oxide nanoparticles for use with the invention. Such a process also provides cerium oxide nanoparticles having an average size down to about 2 nm.

By modifying the process parameters, controlled porosity on the surface of the biocompatible material, acts as scaffolding.

The biocomposite is generally described relative to bone. However, biocomposites according to the invention can also be applied to other types of tissue, such as a tendon, a cartilage, a disk, a meniscus, a muscle, a tooth, a hair, a joint, and a ligament, or a combination thereof.

Ceria Embodiment

As noted above, the biocompatible material preferably comprises a rare earth stabilized zirconia, most preferably being ceria stabilized zirconia. Ceria has been found by the inventors to have advantages over other material for stabilizing zirconia. Of the various zirconia ceramics currently available, ceria stabilized zirconia is the most stable against degradation under humid conditions and against leaching in aqueous environments, including body fluids. In addition, zirconium oxide, when used in conjunction with ceria provides unique oxygen ion conduction properties. To date, ceria stabilized zirconia has been widely used as a coating with excellent catalytic properties, such as a thermal barrier. However, there are no reported applications of ceria-stabilized zirconia for biomedical applications, such as for stem cell growth according to the invention. It should be noted the Ceria-stabilized Zirconia material is a biocompatible material, and the Ceria by itself has been widely used in other biomedical applications as well.

Cerium oxide is largely studied due to its unique properties as oxygen storage material. The valence change $Ce^{+4}$ to $Ce^{+3}$ and vice versa especially in the nanomaterials has been found beneficial for multiple applications of the cerium oxide.

The chemical reaction of the transformation mechanism can be expressed as:

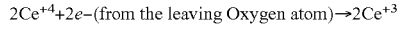
$$2Ce^{+4}+2e\text{–(from the leaving Oxygen atom)}\rightarrow 2Ce^{+3}$$

The mechanism of transformation can be explained with the following: In the $CeO_2$ ($Ce^{+4}$) there are two extra electrons on the Oxygen p-bands. When the oxygen atom leaves (creates vacancy) these two electrons are "left behind". The two electrons from each oxygen atom find the lowest possible empty energy state, which is the f-band of Ce. Each Ce atom acting as a host for the "left behind" Oxygen electrons contribute to the localization of these electrons and each $Ce^{+4}$ with the addition of an electron from the Oxygen atoms may be transformed to the $Ce^{+3}$ ions. Since the vacancy formation in the interior of the particles is considered unstable process, they tend to move more toward the surface.

As noted above, in a preferred embodiment, the biocomposite article is formed using near-net shape nanomanufacturing. In general, using conventional processing, ceramics are sintered from stabilized zirconia powders. The resulting materials generally provide high strength and fracture toughness, but are tough to machine in the dense state. In contrast, porous plasma manufactured near-net-shape ceramics have been found to be relatively easy to machine. The benefits of plasma sprayed ceria-stabilized zirconia are expressed in good corrosion resistance and excellent phase stability at high temperatures. At present, High Isostatic Pressing (HIP), Laser Direct Consolidation, and Plasma Spray Forming (PSF) are considered promising nanomaterial consolidation processes having a few limitations. The disadvantages of the HIP are the size limitation and the complexity of the sample geometry. The inconvenience of the laser process lies in the constraint of material selection. However, one can flow practically all types of materials which can melt in a plasma flame. Plasma Spray Forming (PSF) is a preferred process for the invention since it is one of the most versatile methods of designing large scale nanocomponents with the preferred form and size in minimal time.

The plasma spray gun for plasma spray forming includes a water cooled copper anode and a tungsten cathode. Due to the applied high voltage an arc is created between them. As a result, the flowing gases (Ar and He) reach excessive temperatures, dissociate and ionize to form plasma. Powders are fed into the plasma where they can be melted in a control fashion, accelerated to supersonic speeds, and directed toward a rotating mandrel which is rapidly cooled to form a desired shape and size. Thus, the success of the process lies in the design of the mold mandrel material and the plasma spray parameters, which need to be standardized for each component.

The near-net-shape processing using PSF involves simultaneous control of powder melting and then particle acceleration for deposition on a rotating mandrel or substrate with a proper CTE (coefficient of thermal expansion) to release the parts after cooling. Yet, for the purpose of near-net shape component manufacturing using plasma spray a smooth surface and the correct type material mandrel is of great importance.

In general, the residual stresses generated during plasma spraying are highly dependent of the nature of the sprayed material and the substrate. For example, the difference of the thermal expansion coefficient between the mandrel and the deposited material creates a state of stress in the system. If this stress exceeds the adhesive bonding strength of the coating with the substrate and the cohesive bonding between the particles, the deposition will delaminate from the substrate. However, the inventors use this known "drawback" toward a process known as free-form part manufacturing.

In an embodiment of the invention, a preferably porous biocompatible material has autologous stem cells attached to its surface. The porous nature allows stem cells to be seeded both in the biocompatible material and attached on the surface. Regarding the stem cells, the cells can be whole marrow, isolated stem cells and/or isolated mesenchymal stem cells for repair of segmental defects, spinal fusions or non-unions and other bone defects. Custom cell-matrix implants containing autologous, allogeneic or xenogeneic bone marrow and/or mesenchymal stem cells (MSCs) can be administered using open surgical techniques, arthroscopic techniques or percutaneous injection.

Human mesenchymal stem cells (hMSCs) can be provided as either homogeneous, culture-expanded preparations derived from whole-marrow (or other pre-natal or post-natal source of autologous or allogeneic hMSCs), from hMSC-enriched or heterogeneous cultures containing an effective dose of at least about $10^3$ and preferably at least about $10^5$, preferably about $10^4$ or up to $10^6$, MSCs per milliliter of the composition. In a preferred embodiment, MSC therapy, is to provide that number of enriched or culture-expanded mesenchymal stem cells to the patient, or about the same number in an optimized medium, which repairs the bone or other tissue defect beyond that in a volume of whole marrow equivalent to that of the defect. This is referred to as the "Regenerative MSC Threshold", or that concentration of MSCs necessary to achieve direct repair of the tissue defect. The Regenerative MSC Threshold will vary by: 1) type of tissue (i.e., bone, cartilage, ligament, tendon, muscle, marrow stroma, dermis and other connective tissue); 2) size or extent of tissue defect; 3) formulation with pharmaceutical carrier; and 4) age of the patient.

In one preferred embodiment, the population of stem cells is purified. A purified population of stem cells contains a significantly higher proportion of stem cells than the crude population of cells from which the stem cells are isolated. For example, the purification procedure should lead at least to a five fold increase, preferably at least a ten fold increase, more preferably at least a fifteen fold increase, most preferably at least a twenty fold increase, and optimally at least a twenty-five fold increase in stem cells with respect to the total population. The purified population of stem cells should include at least 15%, preferably at least 20%, more preferably at least 25%, most preferably at least 35%, and optimally at least 50% of stem cells.

Various techniques may be employed to separate the cells by initially removing cells of dedicated lineage. Monoclonal antibodies are particularly useful for identifying markers associated with particular cell lineages and/or stages of differentiation.

If desired, a large proportion of terminally differentiated cells may be removed by initially using a "relatively crude" separation. For example, magnetic bead separations may be used initially to remove large numbers of lineage committed cells. Desirably, at least about 80%, usually at least 70% of the total hematopoietic cells will be removed.

Procedures for separation may include but are not limited to, magnetic separation, using antibody-coated magnetic beads, affinity chromatography, cytotoxic agents joined to a monoclonal antibody or used in conjunction with a monoclonal antibody, including but not limited to, complement and cytotoxins, and "panning" with antibody attached to a solid matrix, e.g., plate, elutriation or any other convenient technique.

Techniques providing accurate separation include but are not limited to, flow cytometry, which can have varying degrees of sophistication, e.g., a plurality of color channels, low angle and obtuse light scattering detecting channels, impedance channels, etc.

In adults, the large majority of pluripotent hematopoietic stem cells are found in the bone marrow. However, small but significant numbers of such cells can be found in the peripheral circulation, liver, spleen and cord blood. Human hematopoietic stem cells for use in the present invention may be derived from human bone marrow, human newborn cord blood, fetal liver or adult human peripheral blood, after appropriate mobilization.

The frequency of hematopoietic stem cells can be dramatically increased by treatment of a subject with certain compounds including cytokines. Such "mobilized" peripheral blood hematopoietic stem cells have become an important alternative to bone marrow-derived hematopoietic stem cells transplantation procedures primarily because engraftment is more rapid. (See, e.g., Tanaka, J, et al., *Int J Hematol* 69(2): 70-4, 1999.)

Such mobilization may be accomplished using for example, one or more of granulocyte colony-stimulating factor (G-CSF), stem cell factor (SCF), thrombopoietin (Tpo), and a chemotherapeutic agent (i.e., cyclophosphamide), or a small molecule, such as AMD 3100, a CXCR4 agonist.

Numerous methods for human hematopoietic stem cell enrichment/isolation are known in the art and generally include obtaining bone marrow, newborn cord blood, fetal liver or adult human peripheral blood which contains hematopoietic stem cells. Once obtained, a hematopoietic stem cell population may be enriched by performing various separation techniques such as density gradient separation, immunoaffinity purification using positive and/or negative selection by panning, FACS or magnetic bead separation. Following such enrichment steps, the cell population is further characterized phenotypically and functionally.

Hematopoietic stem cells (HSC) are initially characterized by immunophenotype, e.g., as lineage negative and either (1) $CD34^+/Thy1^+$ or (2) $CD34^+/CD38^-$ cells that are also $KDR^+$. Human HSC may also be characterized by telomere length, where cells with high proliferative capacity have longer telomeres. In general, a population of cells is considered to be enriched for human HSC if greater than 0.1% of the $CD34^+$ cells have the immunophenotype, $CD34^+$ $CD38^-$ $KDR^+$ or CD34+ Thy1.

Preferred cytokines for the culture of human hematopoietic stem cells include one or more of interleukin-3 (IL-3), interleukin-6 (IL-6), interleukin-11 (IL-11), interleukin-12 (IL-12) stem cell factor (SCF), fms-like tyrosine kinase-3 (flt-3), transforming growth factor-.beta. (TGF-.beta.), an early acting hematopoietic factor, described, for example in WO 91/05795, and thrombopoietin (Tpo).

Human adult hematopoietic stem cells are mostly quiescent or slow cycling. However, it has been demonstrated that when human stem cells are cultured under conditions which include exogenously provided cytokines, wherein TGF-β1 is blocked; quiescent, hematopoietic multipotent progenitors grow in a short term culture assay in which the cells do not grow when TGF-β1 is not blocked.

Molecules used for isolating populations of stem cells are advantageously conjugated with labels that expedite identification and separation. Stem cell specific molecules include, but not limited to: CXCR4, CD 133, SCA-1, Tra-1-60, CD 44, CD 73, CD 90, CD 105 and Stro-1. Examples of labels include magnetic beads; biotin, which may be identified or separated by means of its affinity to avidin or streptavidin; fluorochromes, which may be identified or separated by means of a fluorescence-activated cell sorter (FACS, see below), and the like. Any technique may be used for isolation as long as the technique does not unduly harm the stem cells. Many such methods are known in the art.

In one embodiment, the binding molecule is attached to a solid support. Some suitable solid supports include nitrocellulose, agarose beads, polystyrene beads, hollow fiber membranes, magnetic beads, and plastic Petri dishes. For example, the binding molecule can be covalently linked to Pharmacia Sepharose 6 MB macro beads. The exact conditions and duration of incubation for the solid phase-linked binding molecules with the crude cell mixture will depend upon several factors specific to the system employed, as is well known in the art.

Cells that are bound to the binding molecule are removed from the cell suspension by physically separating the solid support from the remaining cell suspension. For example, the unbound cells may be eluted or washed away with physiologic buffer after allowing sufficient time for the solid support to bind the stem cells. The bound cells are separated from the solid phase by any appropriate method, depending mainly upon the nature of the solid phase and the binding molecule.

For example, bound cells can be eluted by enzymatically "nicking" or digesting an enzyme-sensitive "spacer" sequence between the solid phase and an antibody (e.g., antibodies directed to: CXCR4, CD 133, SCA-1, Tra-1-60, CD 44, CD 73, CD 90, CD 105 and Stro-1). Suitable spacer sequences bound to agarose beads are commercially available from, for example, Pharmacia.

The eluted, enriched fraction of cells may then be washed with a buffer by centrifugation and preserved in a viable state at low temperatures for later use according to conventional technology. The cells may also be used immediately, for example by being infused intravenously into a recipient.

Methods for removing unwanted cells by negative selection are also known. For example, unwanted cells in a starting cell population are labeled by an antibody, or by a cocktail of antibodies, to a cell surface protein characteristic of Lin$^+$ cells. The unwanted antibody-labeled cells are removed by methods known in the art. For example, the labeled cells can be immobilized on a column that binds to the antibodies and captures the cells.

Alternatively, the antibody that binds the cell surface proteins can be linked to magnetic colloids for capture of unwanted cells on a column surrounded by a magnetic field. This system is currently available through StemCell Technologies Inc., Vancouver, British Columbia, Canada. The remaining cells that flow through the column for collection are enriched in cells that do not express the cell surface proteins that the tetrameric antibodies were directed against. The antibody cocktail that can be used to deplete unwanted Lin$^+$ cells can be custom made to include antibodies against lineage specific markers, such as, for example, CD2, CD3, CD4, CD5, CD8, CD10, CD11b, CD13, CD14, CD15, CD16, CD19, CD20, CD24, CD25. CD28, CD29, CD33, CD36, CD38, CD41, CD56, CD66b, CD66e, CD69, and glycophorin A. The desired cells that lack these markers are not lineage committed, i.e. Lin$^-$.

In a preferred embodiment, a labeled binding molecule is bound to the stem cells, and the labeled cells are separated by a mechanical cell sorter that detects the presence of the label. The preferred mechanical cell sorter is a fluorescence activated cell sorter (FACS). FACS machines are commercially available. Generally, the following FACS protocol is suitable for this procedure: a Coulter Epics Eliter sorter is sterilized by running 70% ethanol through the systems. The lines are flushed with sterile distilled water. Cells are incubated with a primary antibody diluted in Hank's balanced salt solution supplemented with 1% bovine serum albumin (HB) for 60 minutes on ice. The cells are washed with HB and incubated with a secondary antibody labeled with fluorescein isothiocyanate (FITC) for 30 minutes on ice. The secondary label binds to the primary antibody. The sorting parameters, such as baseline fluorescence, are determined with an irrelevant primary antibody. The final cell concentration is usually set at one million cells per ml. While the cells are being labeled, a sort matrix is determined using fluorescent beads as a means of aligning the instrument. Once the appropriate parameters are determined, the cells are sorted and collected in sterile tubes containing medium supplemented with fetal bovine serum and antibiotics, usually penicillin, streptomycin and/or gentamicin. After sorting, the cells are re-analyzed on the FACS to determine the purity of the sort.

Any cell can be used in the methods of the invention, including but not limited to, stem cells, thymocytes, precursor cells and the like. A precursor cell population includes cells of a mesodermal derived cellular lineage, more particularly of hematopoietic lineage, bone lineage, endothelial lineage, muscle cell lineage, epithelial cell lineage and neural cell lineage.

A "precursor cell" can be any cell in a cell differentiation pathway that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of erythroid lineage). As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all hematopoietic lineages (e.g., lymphoid, erythroid, and thrombocytic lineages). For example, a pluripotent cell can differ from a totipotent cell by having the ability to develop into all cell lineages except endothelial cells. A "pluripotent population of cells" refers to a composition of cells capable of developing into less than all lineages of cells but at least into all hematopoietic lineages. As such, a totipotent cell or composition of cells is less developed than a pluripotent cell or compositions of cells. As used herein, the terms "develop", "differentiate" and "mature" all refer to the progression of a cell from the stage of having the potential to differentiate into at least two different cellular lineages to becoming a specialized cell. Such terms can be used interchangeably for the purposes of the present application.

As used herein, the term "population" refers to cells having the same or different identifying characteristics. The term "lineage" refers to all of the stages of the development of a cell type, from the earliest precursor cell to a completely mature cell (i.e. a specialized cell).

A stem cell population of the present invention is capable of developing into cells of mesodermal cell lineage, of ectodermal cell lineage or of endodermal cell lineage. As used herein, mesodermal cells include cells of connective tissue, bone, cartilage, muscle, blood and blood vessel, lymphatic and lymphoid organ, notochord, pleura, pericardium, peritoneum, kidney and gonad. Ectodermal cells include epidermal tissue cells, such as those of nail, hair, glands of the skin, the nervous system, the external sense organs (e.g., eyes and ears) and mucous membranes (such as those of the mouth and anus). Endodermal cells include cells of the epithelium such as those of the pharynx, respiratory tract (except the nose), digestive tract, bladder and urethra cells. Preferred cells within a stem cell population of the present invention include cells of at least one of the following cellular lineages: hematopoietic cell lineage, endothelial cell lineage, epithelial cell lineage, muscle cell lineage and neural cell lineage. Other preferred cells within a stem cell population of the present invention include cells of erythroid lineage, endothelial lineage, leukocyte lineage, thrombocyte lineage, erythroid lineage (including primitive and definitive erythroid lineages), macrophage lineage, neutrophil lineage, mast cell lineage, megakaryocyte lineage, natural killer cell lineage, eosinophil lineage, T cell lineage, endothelial cell lineage and B cell lineage.

The biocompatible material may be cultured with any variety of cells. A "cell", according to the present invention, is any preparation of living tissue, including primary tissue explants and preparations thereof, isolated cells, cells lines (including transformed cells), and host cells. Preferably, autologous cells are employed, but xenogeneic, allogeneic, or syngeneic cells are also useful. Where the cells are not autologous, it may be desirable to administer immunosuppressive agents in order to minimize rejection. In preferred embodiments, such agents may be included within the cell composition to ensure effective local concentrations of the agents and to minimize systemic effects of their administration. The cells employed may be primary cells, explants, or cell lines, and may be dividing or non-dividing cells. Cells may be expanded ex-vivo prior to introduction to the biocompatible material. Autologous cells are preferably expanded in this way if a sufficient number of viable cells cannot be harvested from the host.

Any preparation of living cells may be used with the biocompatible material of the present invention. For example, cultured cells or isolated individual cells may be used. Alternatively or additionally, pieces of tissue, including tissue that has some internal structure, may be used. The cells may be primary tissue explants and preparations thereof, cell lines (including transformed cells), or host cells. Where the cells are host cells and are introduced into the biocompatible material in vivo, preferred sources of cells include, but are not limited to, the inner layer of the periosteum or perichondrium, blood or other fluids containing the cells of choice, and damaged host tissue particularly bone or cartilage) that includes such cells.

Any available methods may be employed to harvest, maintain, expand, and prepare cells for use in the present invention. Useful references that describe such procedures include, for example, Freshney, Culture of Animal Cells: a Manual of Basic Technique, Alan R. Liss Inc., New York, N.Y., incorporated herein by reference.

The biocompatible material of the invention is useful as a scaffold for production of hard or soft tissues. Tissue-producing or -degrading cells that may be incorporated into the material include, but are not limited to, chondrocytes, osteocytes, osteoblasts, osteoclasts, mesenchymal stem cells, other bone- or cartilage-producing cells or cell lines, fibroblasts, muscle cells, hepatocytes, parenchymal cells, cells of intestinal origin, nerve cells, and skin cells.

Methods of isolating and culturing such tissue-producing or -degrading cells, and/or their precursors, are known in the art (see, for example, Vacanti et al., U.S. Pat. No. 5,041,138; Elgendy et al., *Biomater.* 14:263, 1993; Laurencin et al, *J. Biomed. Res.* 27:963, 1993; Freed et al., *J. Cell. Biochem.* 51:257, 1993; Atala et al., *J. Urol.* 150:745, 1993; Ishaug et al., *J. Biomed. Mater. Res.* 28:1445, 1994; Chu et al., *J. Biomed. Mater. Res.* 29:1147, 1995; Thomson et al., *J. Biomater. Sci. Polymer Edn.* 7:23, 1995, each of which is incorporated by reference).

For example, mesenchymal stem cells, which can differentiate into a variety of mesenchymal or connective tissues (including, for example, adipose, osseous, cartilagenous, elastic, and fibrous connective tissues), can be isolated, purified, and replicated according to known techniques (see Caplan et al., U.S. Pat. No. 5,486,359; Caplan et al., U.S. Pat. No. 5,226,914; Dennis et al., *Cell Transplantation* 1:23, 1992, each of which is incorporated herein by reference). Such mesenchymal cells have been studied in association with tricalcium phosphate and hydroxyapatite carriers and have been found to be capable of successful differentiation from within such carriers (see Caplan et al., U.S. Pat. No. 5,197,985, incorporated by reference). Similar procedures are employed to direct mesenchymal cell differentiation within biocompatible material scaffolds of the present invention.

The present invention is not limited to the use of tissue-producing cells. Certain preferred embodiments of the invention utilize such cells, primarily because the biocompatible material is so well suited to tissue-regeneration applications (particularly with those involving growth of bone and/or cartilage). Any cell may be cultured or seeded into the biocompatible material of the invention. In some cases, it will be desirable to include other cells in addition with tissue-producing cells.

The cells that are cultured or seeded into the biocompatible material may be genetically engineered, for example to produce a protein or other factor that it useful in the particular application. In preferred embodiments, cells may be engineered to produce molecules that impart resistance to host immune attack and rejection. The Fas-L and CR-1 genes are examples of useful such genes.

In one preferred embodiment, the biocompatible material is coated or pre-treated with cell-adhesion molecules to provide for enhanced cell attachment. Examples of cell adhesive proteins, protein fragments, or peptides, include, but are not limited to fibronectin, laminin, collagen, vitronectin, osteopontin, RGD peptides, RGDS peptides, YIGSR peptides, ICAM-1, PECAM-1, LFA-3, LFA-1, VLA-4, VLA-5, L-Selectin and HCAM. Bone tissue-specific collagen (e.g., Type I collagen) derived from a number of sources are also suitable, including soluble collagen, acid-soluble collagen, collagen soluble in neutral or basic aqueous solutions, as well as those collagens which are commercially available. In addition, Type II collagen, as found in cartilage, also may be used in combination with Type I collagen.

The coating procedure may include the preliminary coating of the biocompatible material with a fibrin matrix, followed by deposition thereon of fibronectin. Alternatively, the fibronectin may be incorporated into the fibrin matrix by depositing a mixture of fibrinogen and fibronectin on the surfaces of the biocompatible material followed by treatment with thrombin to convert fibrinogen to fibrin in situ. In fact, fibrinogen is commonly available from lyophilized cryoprecipitate (obtained during blood protein fractionation) which also contains amounts of fibronectin. Fibrin-fibronectin coatings show good stem cell adhesion.

Further examples of cell-adhesion molecules include: Immunoglobulin Gene Superfamily—ICAM-1 (CD54), LFA-1, PECAM-1 (CD31), LFA-3 (CD58), LFA-2; Integrin Family—$\beta_1$VLA subfamily, VLA-4 (CDw49d/CD29), Fibronectin, VLA-5 (CDw49e/CD29), Fibronectin SAM1, $\beta_2$ leukocyte adhesion subfamily, LFA-1 (CD11a/CD18), ICAM1/2, $\beta_3$ cytoadhesion subfamily, Vitronectin, Vitronectin receptor (CD51/CD61); Selectin Family-L-Selectin, Proteoglycan Analogues, HCAM (CD44), Collagen, Hyaluronic Acid; CD36/LIMP II Family—Thrombospondin, Collagen.

Stem Cell Compositions

In a preferred embodiment, the isolated stem cells are contacted with a vector expressing a desired molecule. The molecule can be a growth factor, chemokine, cell specific maturation factor, cell differentiation factor and the like. Examples of genes useful for introduction into isolated stem cells include those that encode bone morphogenic proteins such as OP-1, OP-2, OP-3, COP-1, COP-3, COP-4, COP-5, COP-7, COP-16, BMP-2, BMP-3, BMP-3b, MP-4, BMP-5, BMP-6, BMP-9, BMP-10, BMP-11, BMP-12, BMP-13, BMP-14, B-15, BMP-16, BMP-17, BMP-18, GDF-1, GDF-2, GDF-3, GDF-5, GDF-6, GDF-7, GDF-8, GDF-9, GDF-10, GDF-11, GDF-12, MP121, dorsalin-1, DPP, Vg-1, Vgr-1, 6A protein, NODAL, UNIVIN, SCREW, ADMP, NEURAL, TGF-$\beta$ and conservative amino acid sequence variants thereof having osteogenic activity. Other examples of desired molecules include: Factor VIII, von Willebrand factor, insulin, tissue plasminogen activator, any of the interleukins, or a growth factor. Some examples of interleukins include IL-1, -2, -3, -4, -5, -6, -7, -8, -9, -10, -11, -12, -13, -14, -15, -16, -17, -18, -19, -20, and -21. Some examples of suitable growth factors include erythropoietin, thrombopoietin, PDGF, G-CSF, GM-CSF, IGF, TGFβ, VEGF, LIF, CNTF, FGF, EGF and BMP (bone morphogenic protein).

The stem cells can be transiently transduced, transduced with a stably integrated vector or a self-replicating extrachromosomal vector.

In another preferred embodiment, integration of a vector into the stem cell genome is avoided. Lack of integration into the stem cell genome is accomplished by using plasmid DNA or messenger RNA. As an illustrative example, the expression of the endogenous gene within the stem cell genome is activated using either small molecules derived from a chemical library and screened for specific activation of the desired gene and/or adding a recombinant protein or peptide that transcriptionally activates the expression of the homing protein. The transcriptional activation can use any transcriptional activator, for example, a zinc finger-transcription activator (additional DNA binding protein motifs include helix-turn-helix and leucine zipper) fusion protein or a specific transcription activator protein that binds to the enhancer or promoter region responsible for controlling expression of the homing protein. Examples of homing genes that could influence differentiation include but not limited to: SCG 10; Na Channel II; glut-2, synapsin, epo, SCF, shh, wint, BMPs Ephrins, Pax-6, Emx-2, Mash-1, jagged 1 and 2, notch- and 2, ephrin B2 and ephrin B4, Bmi-1, different homeobox genes HOXB4 that regulates the probability of stem cell renewal. Bmi-1 is expressed in stem cells and is essential for their maintenance.

In another preferred embodiment, a gene delivery vehicle comprises use of a non-integrating vector. By gene delivery vehicle is meant a carrier which can deliver at least one nucleic acid to a host cell. The nucleic acid that is delivered to a host cell may comprise a nucleic acid sequence encoding an amino acid sequence, such as for example, Factor VIII, Factor IX, or mutant genes for β-glucocerebrosidase, erythropoietin ("EPO"), α-L-iduronidase, iduronate sulphatase, N-sulphatase, N-acetyl α-D-glucosaminidase, α-glucosamine-N-acetyltransferase, N-acetyl-α-D-glucosaminide-6-sulphatase, Galactosamine-6 sulphate sulphatase, β-galactosidase, N-acetyl-alactosamine-4-sulphatase, acid ceraminidase, acid sphingomyelinase, galactocerebroside β-galactosidase, arylsuphatase A, adenosine deaminase, α-L-fucosidase growth factors such as the interleukin family, angiogenesis stimulating or inhibiting factors such as the nitric oxide synthases (NOS1-3), vascular endothelial growth factors ("VEGF"), Angiostatin 1-7. Other examples of genes useful for introduction into isolated stem cells include those that encode Factor VIII, von Willebrand factor, insulin, tissue plasminogen activator, any of the interleukins, or a growth factor. Some examples of interleukins include IL-1, -2, -3, -4, -5, -6, -7, -8, -9, -10, -11, -12, -13, -14, -15, -16, -17, -18, -19, -20, and -21. Some examples of suitable growth factors include erythropoietin, thrombopoietin, PDGF, G-CSF, GM-CSF, IGF, TGFβ, VEGF, LIF, CNTF, FGF, EGF and BMP (bone morphogenic protein). Examples of bone morphogenic proteins include, but not limited to: OP-1, OP-2, OP-3, COP-1, COP-3, COP-4, COP-5, COP-7, COP-16, BMP-2, BMP-3, BMP-3b, MP-4, BMP-5, BMP-6, BMP-9, BMP-10, BMP-11, BMP-12, BMP-13, BMP-14, B-15, BMP-16, BMP-17, BMP-18, GDF-1, GDF-2, GDF-3, GDF-5, GDF-6, GDF-7, GDF-8, GDF-9, GDF-10, GDF-11, GDF-12, MP121, dorsa-lin-1, DPP, Vg-1, Vgr-1, 6 A protein, NODAL, UNIVIN, SCREW, ADMP, NEURAL, TGF-β and conservative amino acid sequence variants thereof having osteogenic activity. The nucleic acid may further comprise at least one promoter, and/or enhancer, and/or terminator. It may also comprise transcription initiation sites, and the like. By delivering a nucleic acid to a host cell, the nucleic acid is moved from the outside to the inside of the host cell. Transient expression of the transgene is sufficient to trigger cells to differentiate into the desired mature tissue cells. Therefore, a preferred non-integrating vector is adenovirus (adenovirus has other affects on the cells, such as immunostimulatory properties that may results in elimination of the infected cell.) or non-replicating, non-integrating plasmids.

A non-replicating, non-integrating plasmid is a nucleic acid which when transfected into a host cell does not replicate and does not specifically integrate into the host cell's genome (i.e. does not integrate at high frequencies and does not integrate at specific sites). In other preferred embodiments, the plasmid is non-integrating but does replicate and can be used in those instances where larger numbers of transduced cells are required.

Replicating plasmids can be identified using standard assays including the standard replication assay of Ustav et al., *EMBO J.*, 10, 449-457, 1991. A potential stabilized episome plasmid is derived from the Epstein bar virus gene, EBNA-1, that causes the plasmid to exist as an episome but is limited to B cell lineages.

In other preferred embodiments, a non-replicating, non-integrating plasmid is used. This type of plasmid cannot be stably maintained in cells, independently of genomic DNA replication, and which does not persist in progeny cells for three or more cell divisions without a significant loss in copy number of the plasmid in the cells, i.e., with a loss of greater than an average of about 50% of the plasmid molecules in progeny cells between a given cell division. Generally, in self-replicating vectors, the self-replicating function is provided by using a viral origin of replication and providing one or more viral replication factors that are required for replication mediated by that particular viral origin. The term "transiently transfecting, non-integrating plasmid" herein means the same as the term "non-replicating, non-integrating plasmid" as defined above.

Preferably the plasmid is a naked nucleic acid. As used herein, the term "naked" refers to a nucleic acid molecule that is free of direct physical associations with proteins, lipids, carbohydrates or proteoglycans, whether covalently or through hydrogen bonding. The term does not refer to the presence or absence of modified nucleotides or ribonucleotides, or chemical modification of the all or a portion of a nucleic acid molecule by such means as methylation or the inclusion of protecting groups or cap- or tail structures.

In a preferred embodiment, a non-integrating vector comprises a nucleic acid encoding for any one of: Factor VIII, Factor IX, or mutant genes for β-glucocerebrosidase, erythropoietin ("EPO"), α-L-iduronidase, iduronate sulphatase, N-sulphatase, N-acetyl α-D-glucosaminidase, α-glucosamine-N-acetyltransferase, N-acetyl-α-D-glucosaminide-6-sulphatase, Galactosamine-6 sulphate sulphatase, β-galactosidase, N-acetyl-alactosamine-4-sulphatase, acid ceraminidase, acid sphingomyelinase, galactocerebroside β-galactosidase, arylsuphatase A, adenosine deaminase, α-L-fucosidase growth factors such as the interleukin family, angiogenesis stimulating or inhibiting factors such as the nitric oxide synthases (NOS1-3), vascular endothelial growth factors ("VEGF"), Angiostatin 1-7. Other examples of genes useful for introduction into isolated stem cells include those that encode Factor VIII, von Willebrand factor, insulin, tissue plasminogen activator, any of the interleukins, or a growth factor. Some examples of interleukins include IL-1, -2, -3, -4, -5, -6, -7, -8, -9, -10, -11, -12, -13, -14, -15, -16, -17, -18, -19, -20, and -21. Some examples of suitable growth factors include erythropoietin, thrombopoietin, PDGF, G-CSF, GM-CSF, IGF, TGFβ, VEGF, LIF, CNTF, FGF, EGF and BMP (bone morphogenic protein). Examples of bone morphogenic proteins include, but not limited to: OP-1, OP-2, OP-3, COP-1, COP-3, COP-4, COP-5, COP-7, COP-16, BMP-2, BMP-3, BMP-3b, MP-4, BMP-5, BMP-6, BMP-9, BMP-10, BMP-11, BMP-12, BMP-13, BMP-14, B-15, BMP-16, BMP-17, BMP-18, GDF-1, GDF-2, GDF-3, GDF-5, GDF-6, GDF-7, GDF-8, GDF-9, GDF-10, GDF-11, GDF-12, MP 121, dorsalin-1, DPP, Vg-1, Vgr-1, 6 A protein, NODAL, UNIVIN, SCREW, ADMP, NEURAL, TGF-β and conservative amino acid sequence variants thereof having osteogenic activity. In certain embodiments, the vector comprises nucleic acids expressing targeting agents. For example, targeting agents may include, but are not limited to, EGF, FGF, SDF-1, transferrin, and endothelial specific peptides and bone specific ligands or antibodies to cell surface markers, such as CD34.

In another non-limiting example, a targeting agent may comprise an antibody, cytokine, growth factor, hormone, lymphokine, receptor protein, such as, for example CD4 (T-helper cell surface marker), CD8 (cytotoxic lymphocyte cell surface marker) or soluble fragments thereof, a nucleic acid which bind corresponding nucleic acids through base pair complementarity, or a combination thereof (U.S. Pat. No. 6,071,533, incorporated herein by reference). In other embodiments, the targeting ligand may comprise a cellular receptor-targeting ligand, a fusogenic ligand, a nucleus targeting ligand, or a combination thereof (U.S. Pat. No. 5,908,777, incorporated herein by reference). In another non-limiting example, the targeting ligand may comprise an integrin receptor ligand, described in U.S. Pat. No. 6,083,741, incorporated herein by reference.

In another preferred embodiment, the vector integrates into the stem cell genome. Preferably the vector expresses SCG 10; Na Channel II; glut-2, synapsin, epo, SCF, shh, wint, BMPs Ephrins, Pax-6, Emx-2, Mash-1, jagged 1 and 2, notch-and 2, ephrin B2 and ephrin B4, Bmi-1, HOXB4, Factor VIII, Factor IX, or mutant genes for β-glucocerebrosidase, erythropoietin ("EPO"), α-L-iduronidase, iduronate sulphatase, N-sulphatase, N-acetyl α-D-glucosaminidase, α-glucosamine-N-acetyltransferase, N-acetyl-α-D-glucosaminide-6-sulphatase, Galactosamine-6 sulphate sulphatase, β-galactosidase, N-acetyl-alactosamine-4-sulphatase, acid ceraminidase, acid sphingomyelinase, galactocerebroside β-galactosidase, arylsuphatase A, adenosine deaminase, α-L-fucosidase growth factors such as the interleukin family, angiogenesis stimulating or inhibiting factors such as the nitric oxide synthases (NOS1-3), vascular endothelial growth factors ("VEGF"), Angiostatin 1-7. Other examples of genes useful for introduction into isolated stem cells include those that encode Factor VIII, von Willebrand factor, insulin, tissue plasminogen activator, any of the interleukins, or a growth factor. Some examples of interleukins include IL-1, -2, -3, -4, -5, -6, -7, -8, -9, -10, -11, -12, -13, -14, -15, -16, -17, -18, -19, -20, and -21. Some examples of suitable growth factors include erythropoietin, thrombopoietin, PDGF, G-CSF, GM-CSF, IGF, TGFβ, VEGF, LIF, CNTF, FGF, EGF and BMP (bone morphogenic protein) and the integration is site-specific. Examples of bone morphogenic proteins include, but not limited to: OP-1, OP-2, OP-3, COP-1, COP-3, COP-4, COP-5, COP-7, COP-16, BMP-2, BMP-3, BMP-3b, MP-4, BMP-5, BMP-6, BMP-9, BMP-10, BMP-11, BMP-12, BMP-13, BMP-14, B-15, BMP-16, BMP-17, BMP-18, GDF-1, GDF-2, GDF-3, GDF-5, GDF-6, GDF-7, GDF-8, GDF-9, GDF-10, GDF-11, GDF-12, MP121, dorsalin-1, DPP, Vg-1, Vgr-1, 6 A protein, NODAL, UNIVIN, SCREW, ADMP, NEURAL, TGF-β and conservative amino acid sequence variants thereof having osteogenic activity.

Introducing the genes, fragments or variants thereof, into an individual can include use of vectors, liposomes, naked DNA, adjuvant-assisted DNA, gene gun, catheters, etc. Vectors include chemical conjugates such as described in WO 93/04701, which has a targeting moiety (e.g. a ligand to a cellular surface receptor), and a nucleic acid binding moiety (e.g. polylysine), viral vector (e.g. a DNA or RNA viral vector), fusion proteins such as described in PCT/US95/02140 (WO 95/22618) which is a fusion protein containing a target moiety (e.g. an antibody specific for a target cell) and a nucleic acid binding moiety (e.g. a protamine), plasmids, phage etc.

When taken up by a cell, the genetic construct(s) remain present in the cell as a functioning extrachromosomal molecule. DNA may be introduced into cells where it remains as separate genetic material in the form of a plasmid or plasmids. Alternatively, RNA may be administered to the cell. It is also contemplated to provide the genetic construct as a linear minichromosome including a centromere, telomeres and an origin of replication.

Vectors can include regulatory elements necessary for gene expression of a nucleic acid molecule. The elements include: a promoter, an initiation codon, a stop codon, and a polyadenylation signal. In addition, enhancers may be required for gene expression of the sequence of choice, variants or fragments thereof. It is necessary that these elements are operably linked to the sequence that encodes the desired proteins and that the regulatory elements are operable in the individual to whom they are administered.

Initiation codons and stop codons are generally considered to be part of a nucleotide sequence that encodes the desired tissue specific protein. However, it is necessary that these elements are functional in the individual to whom the gene construct is administered. The initiation and termination codons must be in frame with the coding sequence.

Promoters and polyadenylation signals used must be functional within the cells of the individual. Examples of promoters useful to practice the present invention, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metallothionein. Examples of polyadenylation signals useful to practice the present invention, especially in the production of a genetic vaccine for humans, include but are not limited to SV40 polyadenylation signals and LTR polyadenylation signals, human growth hormone poly A signal. In particular, the SV40 polyadenylation signal which is in pCEP4 plasmid (Invitrogen, San Diego Calif.), referred to as the SV40 polyadenylation signal, can be used.

In addition to the regulatory elements required for DNA expression, other elements may also be included in the DNA molecule. Such additional elements include, zinc fingers, enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. For example, plasmids pCEP4 and pREP4 from Invitrogen (San Diego, Calif.) contain the Epstein Barr virus origin of replication and nuclear antigen EBNA-1 coding region which produces high copy episomal replication without integration.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs which are functional in the cells.

In some embodiments, the nucleic acid molecule is delivered to the cells in conjunction with administration of a facilitating agent. Facilitating agents are also referred to as polynucleotide function enhancers or genetic vaccine facilitator agents. Facilitating agents are described in e.g. International Application No. PCT/US94/00899 filed Jan. 26, 1994 and International Application No. PCT/US95/04071 filed Mar. 30, 1995, both incorporated herein by reference. Facilitating agents which are administered in conjunction with nucleic acid molecules may be administered as a mixture with the nucleic acid molecule or administered separately simultaneously, before or after administration of nucleic acid molecules.

In some preferred embodiments, the genetic constructs of the invention are formulated with or administered in conjunction with a facilitator selected from the group consisting of, for example, benzoic acid esters, anilides, amidines, urethans and the hydrochloride salts thereof such as those of the family of local anesthetics. The facilitating agent is administered prior to, simultaneously with or subsequent to the genetic construct. The facilitating agent and the genetic construct may be formulated in the same composition.

In some embodiments, the genetic constructs are administered free of facilitating agents, that is in formulations free from facilitating agents using administration protocols in which the genetic constructions are not administered in conjunction with the administration of facilitating agents. (cationic lipid/helper lipid formulations, electroporation, ultrasound, cationic polymers (PEI, poly lysine, poly-L-ornithine), non-interacting polymers, such as Poloxamer or polyvinylpyrolidone).

Nucleic acid molecules which are delivered to cells according to the invention may serve as genetic templates for proteins that function as tissue specific maturation agents. In preferred embodiments, the nucleic acid molecules comprise the necessary regulatory sequences for transcription and translation of the coding region in the cells of the animal.

Additionally, the nucleic acid sequences of choice can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson et al., 1978, *J. Biol. Chem.* 253: 6551; Zoller and Smith, 1984, *DNA* 3:479-488; Oliphant et al., 1986, *Gene* 44: 177; Hutchinson et al., 1986, *Proc. Natl. Acad. Sci. U.S.A.* 83: 710; and others). PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

Various methods known to those skilled in the art can be used to express nucleic acid sequences in the non-immortalized cells. For example, the identified and isolated gene can be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector that has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2μ plasmid.

Another method comprises ligating the differentiation protein into an artificial replicating chromosome and microinject it into the stem cell. The percent of transformed cells may not be important because the disease state selects for the transformed stem cell. Larger numbers of stem cells may be transduced if a critical mass is needed to seed the tissue replacement or tissue correction site.

In an alternative method, the desired gene may be identified and isolated after insertion into a suitable cloning vector in a "shot gun" approach. Enrichment for the desired gene, for example, by size fractionation, removal of highly-repetitive sequences, subtractive or otherwise selective hybridization, and other methods as may be known in the art, can be done before insertion into the cloning vector.

The nucleotide sequence can be inserted into an appropriate expression vector, i.e., a vector which contains the necessary elements for the transcription and translation of the inserted protein-coding sequence. Such elements are termed herein a "promoter." Thus, the nucleic acid encoding a desired protein, functional fragments, derivatives or analogs thereof, is operationally associated with a promoter in an expression vector of the invention. Both cDNA and genomic sequences can be cloned and expressed under control of such regulatory sequences. An expression vector also preferably includes a replication origin. The necessary transcriptional and translational signals can be provided on a recombinant expression vector.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant protein, may be expressed chromosomally, after integration of the coding sequence by recombination. In this regard, any of a number of amplification systems may be used to achieve high levels of stable gene expression (See Sambrook et al., 1989, supra).

Numerous techniques are known and are useful according to the invention for delivering the vectors described herein to cells, including the use of nucleic acid condensing agents, electroporation, complexation with asbestos, polybrene, DEAE cellulose, Dextran, liposomes, cationic liposomes, lipopolyamines, polyornithine, particle bombardment and direct microinjection (reviewed by Kucherlapati and Skoultchi, *Crit. Rev. Biochem.* 16:349-379 (1984); Keown et al., *Methods Enzymol.* 185:527 (1990)).

A vector of the invention may be delivered to a host cell via a viral or non-viral means of delivery. Preferred delivery methods of viral origin include viral particle packaging cell lines as transfection recipients for the vector of the present invention into which viral packaging signals have been engineered, such as those of adenovirus, herpes viruses and papovaviruses. Preferred non-viral based gene delivery means and methods may also be used in the invention and include direct naked nucleic acid injection, nucleic acid condensing peptides and non-peptides, cationic liposomes and encapsulation in liposomes.

Methods for constructing and using viral vectors are known in the art [see, e.g., Miller and Rosman, *BioTechniques* 7:980-990 (1992)]. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsulating the viral particles.

DNA viral vectors include an attenuated or defective DNA virus, such as but not limited to adenovirus, adeno-associated virus (AAV), herpes simplex virus (HSV), papillomavirus, Epstein-Barr virus (EBV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Examples of particular vectors include, but are not limited to, a defective herpes virus 1 (HSVI) vector [Kaplitt et al., Molec. Cell. Neurosci. 2:320-330 (1991)], defective herpes virus vector lacking a glycoprotein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Stratford-Perricaudet et al. [*J. Clin. Invest.* 90:626-630 (1992); see also La Salle et al., *Science* 259:988-990 (1993)]; and a defective adeno-associated virus vector [Samulski et al., *J. Virol.* 61:3096-3101 (1987); Samulski et al., *J. Virol.* 63:3822-3828 (1989); Lebkowski et al., *Mol. Cell. Biol.* 8:3988-3996 (1988)].

Adenoviris vectors: in one preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mavl, Beard 75 (1990) 81), ovine, porcine, avian, and simian (example: SAV) origin. The adenovirus of animal origin is a canine adenovirus, more preferably a CAV2 adenovirus (e.g., Manhattan or A26/61 strain (ATCC VR-800), for example). Adenovirus vectors, adeno-associated virus vectors, parvovirus vectors and herpes simplex virus vectors are preferred for introducing the nucleic acid e.g. SCG 10; Na Channel II; glut-2, synapsin, epo, SCF, shh, wint, BMPs Ephrins, Pax-6, Emx-2, Mash-1, jagged 1 and 2, notch- and 2, ephrin B2 and ephrin B4, Bmi-1, different homeobox genes HOXB4. The adenovirus vector results in a shorter term expression (about 2 months) than adeno-associated virus (about 4 months), which in turn is shorter than HSV vectors. The vectors can be introduced by standard techniques, e.g. infection, transfection, transduction or transformation. Examples of modes of gene transfer include for example, naked DNA calcium phosphate precipitation, DEAE dextran, electroporation, protoplast fusion, lipofection, cell microinjection and viral vectors.

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94/12649 and WO95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (Levrero et al., *Gene* 101 (1991) 195, EP 185 573; Graham, *EMBO J.* 3 (1984) 2917). In particular, they can be prepared by homologous recombination between an adenovirus or modified adenovirus genome and a plasmid which carries, inter alia, the DNA sequence of interest. The homologous recombination is effected following cotransfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., *J. Gen. Virol.* 36 (1977) 59) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

Adeno-associated viruses. In a preferred embodiment, the vector is an adeno-associated viruses. The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions which carry the encapsidation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques. The invention also relates, therefore, to an AAV-derived recombinant virus whose genome encompasses a sequence encoding a nucleic acid encoding a tissue maturation factor, (e.g. SCG 10; Na Channel II; glut-2, synapsin, epo, SCF, shh, wint, BMPs Ephrins, Pax-6, Emx-2, Mash-1, jagged 1 and 2, notch- and 2, ephrin B2 and ephrin B4, Bmi-1, different homeobox genes, such as, HOXB4), flanked by the AAV ITRs; Factor VIII, Factor IX, or mutant genes for β-glucocerebrosidase, erythropoietin ("EPO"), Q-L-iduronidase, iduronate sulphatase, N-sulphatase, N-acetyl α-D-glucosaminidase, α-glucosamine-N-acetyltransferase, N-acetyl-α-D-glucosaminide-6-sulphatase, Galactosamine-6 sulphate sulphatase, β-galactosidase, N-acetylalactosamine-4-sulphatase, acid ceraminidase, acid sphingomyelinase, galactocerebroside β-galactosidase, arylsuphatase A, adenosine deaminase, α-L-fucosidase growth factors such as the interleukin family, angiogenesis stimulating or inhibiting factors such as the nitric oxide synthases (NOS1-3), vascular endothelial growth factors ("VEGF"), Angiostatin 1-7. Other examples of genes useful for introduction into isolated stem cells include those that encode Factor VIII, von Willebrand factor, insulin, tissue plasminogen activator, any of the interleukins, or a growth factor. Some examples of interleukins include IL-1, -2, -3, -4, -5, -6, -7, -8, -9, -10, -11, -12, -13, -14, -15, -16, -17, -18, -19, -20, and -21. Some examples of suitable growth factors include erythropoietin, thrombopoietin, PDGF, G-CSF, GM-CSF, IGF, TGFβ, VEGF, and BMP (bone morphogenic protein). The invention also relates to a plasmid encompassing a sequence encoding a nucleic acid encoding a desired gene flanked by two ITRs from an AAV. Such a plasmid can be used as it is for transferring the nucleic acid sequence, with the plasmid, where appropriate, being incorporated into a liposomal vector (pseudo-virus).

Retrovirus vectors: in another embodiment the gene can be introduced in a retroviral vector, e.g., as described in Anderson et al., U.S. Pat. No. 5,399,346; Mann et al., 1983, *Cell* 33:153; Temin et al., U.S. Pat. No. 4,650,764; Temin et al., U.S. Pat. No. 4,980,289; Markowitz et al., 1988, *J. Virol.* 62:1120; Temin et al., U.S. Pat. No. 5,124,263; EP 453242, EP178220; Bernstein et al. *Genet. Eng.* 7 (1985) 235; McCormick, *BioTechnology* 3 (1985) 689; International Patent Publication No. WO 95/07358, published Mar. 16, 1995, by Webster, K. A., Kubasiak, L. A., Prentice, H. and Bishopric, N. H.: Stable germline transmission of a hypoxia-activated molecular gene switch. From the double helix to molecular medicine, (ed. W. J. Whelan et al.), Oxford University Press, (2003); and Kuo et al., 1993, *Blood* 82:845. The retroviruses are integrating viruses which infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsidation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+ envAm-12 cell line (WO89/07150). In addition, the recombinant retroviral vectors can contain modifications within the LTRs for suppressing transcriptional activity as well as extensive encapsidation sequences which may include a part of the gag gene (Bender et al., *J. Virol.* 61 (1987) 1639). Recombinant retroviral vectors are purified by standard techniques known to those having ordinary skill in the art.

Retroviral vectors can be constructed to function as infectious particles or to undergo a single round of transfection. In the former case, the virus is modified to retain all of its genes except for those responsible for oncogenic transformation properties, and to express the heterologous gene. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional virus. Targeted gene delivery is described in International Patent Publication WO 95/28494, published October 1995.

Lentiviral Vectors: lentiviruses include members of the bovine lentivirus group, equine lentivirus group, feline lentivirus group, ovinecaprine lentivirus group and primate lentivirus group. The development of lentiviral vectors for gene therapy has been reviewed in Klimatcheva et al., 1999, *Frontiers in Bioscience* 4: 481-496. The design and use of lentiviral vectors suitable for gene therapy is described, for example, in U.S. Pat. No. 6,207,455, issued Mar. 27, 2001, and U.S. Pat. No. 6,165,782, issued Dec. 26, 2000. Examples of lentiviruses include, but are not limited to, HIV-1, HIV-2, HIV-1/HIV-2 pseudotype, HIV-1I/SIV, FIV, caprine arthritis encephalitis virus (CAEV), equine infectious anemia virus and bovine immunodeficiency virus. HIV-1 is preferred.

Autonomous parvoviruses are small DNA viruses that replicate autonomously in rapidly dividing cells. The genomes of autonomous parvoviruses do not integrate, at least not at a detectable level. Autonomous parvovirus genomes are single-stranded DNA molecules about 5 kilobases (kb) in size. The genomes are organized such that the NS gene encoding the nonstructural polypeptides NS1 and NS2 is located on the left side of the genome and the VP gene encoding the structural polypeptides required for capsid formation are on the right side of the genome. Expression of the nonstructural polypeptides is controlled by a transcription control sequence called P4 in most parvoviruses, which is located at about map unit position 4 of the genome (assuming the entire genome is 100 map units and numbering is from left to right). Expression of the structural polypeptides is controlled by a transcription control sequence called P38, P39 or P40 in most parvoviruses, which is located at about map unit position 38 to about 40, depending on the autonomous parvovirus. NS 1 serves as a trans-activator of the latter transcription control sequence. NS 1 is also essential for virus replication and appears to be the primary mediator of parvovirus cytotoxicity, particularly against tumor cells. Autonomous parvovirus genomes also have inverted repeat sequences (i.e., palindromes) at each end which contain essential signals for replication and encapsidation of the virus. There have been several studies on the mechanisms of autonomous parvovirus replication, gene expression, encapsidation, and cytotoxicity. See, for example, Sinkovics, pp. 1281-1290, 1989, Anticancer Res., Vol 9.

Suitable autonomous parvovirus nucleic acid sequences include, but are not limited to, LuIII parvovirus (LuIII), minute virus of mice (MVM; e.g., MVMi and MVMp), hamster parvovirus (e.g., HI), feline panleukopenia virus, canine parvovirus, porcine parvovirus, latent rat virus, mink enteritis virus, human parvovirus (e.g., B 19), bovine parvovirus, and Aleutian mink disease parvovirus nucleic acid sequences. LuIII parvovirus is a parvovirus of unknown origin that was isolated as a contaminant of a substrain of human permanent cell line Lu106. The LuIII parvovirus exhibits high infectivity.

Non-viral Vectors: alternatively, the vector can be introduced in vivo as nucleic acid free of transfecting excipients, or with transfection facilitating agents, e.g., lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Feigner, et. al., *Proc. Natl. Acad. Sci. U.S.A.* 84:7413-7417 (1987); see Mackey, et al., *Proc. Natl Acad. Sci. U.S.A.* 85:8027-8031 (1988); Ulmer et al., *Science* 259:1745-1748 (1993)]. The use of cationic lipids may promote encapsulation of negatively charged nucleic acids, and also promote fusion with negatively charged cell membranes [Feigner and Ringold, *Science* 337:387-388 (1989)]. Particularly useful lipid compounds and compositions for transfer of nucleic acids are described in International Patent Publications WO95/18863 and WO96/17823, and in U.S. Pat. No. 5,459,127. Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

Naked DNA vectors can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963-967 (1992); Wu and Wu, *J. Biol. Chem.* 263: 14621-14624 (1988); Williams et al., *Proc. Natl. Acad. Sci. USA* 88:2726-2730 (1991)]. Receptor-mediated DNA delivery approaches can also be used [Curiel et al., Hum. Gene Ther. 3:147-154(1992); Wu and Wu, *J Biol. Chem.* 262:4429-4432 (1987)]. Methods for formulating and administering naked DNA to mammalian muscle tissue are disclosed in U.S. Pat. Nos. 5,580,859 and 5,589,466, the contents of which are incorporated herein by reference.

Regulatory Regions: expression of, for example, SCG 10; Na Channel II; glut-2, synapsin, epo, SCF, shh, wint, BMPs Ephrins, Pax-6, Emx-2, Mash-1, jagged 1 and 2, notch- and 2, ephrin B2 and ephrin B4, Bmi-1, different homeobox genes, such as, HOXB4, from a vector of the invention may be controlled by any regulatory region, i.e., promoter/enhancer element known in the art. Examples also include, Factor VIII, Factor IX, or mutant genes for β-glucocerebrosidase, erythropoietin ("EPO"), α-L-iduronidase, iduronate sulphatase, N-sulphatase, N-acetyl α-D-glucosaminidase, α-glucosamine-N-acetyltransferase, N-acetyl-α-D-glucosaminide-6-sulphatase, Galactosamine-6 sulphate sulphatase, β-galactosidase, N-acetyl-alactosamine-4-sulphatase, acid ceraminidase, acid sphingomyelinase, galactocerebroside β-galactosidase, arylsuphatase A, adenosine deaminase, α-L-fucosidase growth factors such as the interleukin family, angiogenesis stimulating or inhibiting factors such as the nitric oxide synthases (NOS1-3), vascular endothelial growth factors ("VEGF"), Angiostatin 1-7. Other examples of genes useful for introduction into isolated stem cells include those that encode Factor VIII, von Willebrand factor, insulin, tissue plasminogen activator, any of the interleukins, or a growth factor. Some examples of interleukins include IL-1, -2, -3, -4, -5, -6, -7, -8, -9, -10, -11, -12, -13, -14, -15, -16, -17, -18, -19, -20, and -21. Some examples of suitable growth factors include erythropoietin, thrombopoietin, PDGF, G-CSF, GM-CSF, IGF, TGFβ, VEGF, and BMP (bone morphogenic protein). The regulatory regions may comprise a promoter region for functional transcription in the tissue of interest, as well as a region situated in 3' of the gene of interest, and which specifies a signal for termination of transcription and a polyadenylation site. All these elements constitute an expression cassette.

Promoters that may be used in the present invention, include both constitutive promoters and regulated (inducible) promoters. The promoter may be naturally responsible for the expression of the nucleic acid. It may also be from a heterologous source. In particular, it may be promoter sequences of eukaryotic or viral genes. For example, it may be promoter sequences derived from the genome of the cell which it is desired to infect. Likewise, it may be promoter sequences derived from the genome of a virus, including the adenovirus used. In this regard, there may be mentioned, for example, the promoters of the E1A, MLP, CMV and RSV genes and the like.

In addition, the promoter may be modified by addition of activating or regulatory sequences or sequences allowing a tissue-specific or predominant expression (enolase and GFAP promoters and the like). Moreover, when the nucleic acid does not contain promoter sequences, it may be inserted, such as into the virus genome downstream of such a sequence. Some promoters useful for practice of this invention are heat shock protein promoters (hsp), ubiquitous promoters (e.g., HPRT, vimentin, actin, tubulin), intermediate filament promoters (e.g., GFAP, desmin, neurofilaments, keratin), therapeutic gene promoters (e.g., MDR type, CFTR, factor VIII), tissue-specific promoters (e.g., actin promoter in smooth muscle cells), promoters which are preferentially activated in dividing cells, promoters which respond to a stimulus (e.g., steroid hormone receptor, retinoic acid receptor), tetracycline-regulated transcriptional modulators, cytomegalovirus immediate-early, retroviral LTR, metallothionein, SV-40, E1A, and MLP promoters. Tetracycline-regulated transcriptional modulators and CMV promoters are described in WO 96/01313, U.S. Pat. Nos. 5,168,062 and 5,385,839, the contents of which are incorporated herein by reference.

Thus, the promoters which may be used to control gene expression include, but are not limited to, GFAP, HSP promoters, the cytomegalovirus (CMV) promoter, the SV40 early promoter region (Benoist and Chambon, 1981, *Nature* 290:304-310), the promoter contained in the 3' long terminal repeat of Rous sarcoma virus (Yamamoto, el al., 1980, *Cell* 22:787-797), the herpes thynidine kinase promoter (Wagner et al., 1981, Proc. NatL. Acad. Sci. U.S.A. 78:1441-1445), the regulatory sequences of the metallothionein gene (Brinster et al., 1982, *Nature* 296:39-42); prokaryotic expression vectors such as the β-lactamase promoter (Villa-Kamaroff, et al., 1978, *Proc. NatL. Acad. Sci. U.S.A.* 75:3727-3731), or the tac promoter (DeBoer, et al., 1983, *Proc. Natl. Acad. Sci. U.S.A.* 80:21-25); promoter elements from yeast or other fungi such as the Gal 4 promoter, the ADC (alcohol dehydrogenase) promoter, PGK (phosphoglycerol kinase) promoter, alkaline phosphatase promoter.

Various peptides derived from the amino acid sequences of viral envelope proteins have been used in gene transfer when co-administered with polylysine DNA complexes (Plank et al., *J. Biol. Chem.* 269:12918-12924 (1994)); Trubetskoy et al., *Bioconjugate Chem.* 3:323(1992); WO 91/17773; WO 92/19287; and Mack et al., Am. J Med. Sci. 307:138-143 (1994)) suggest that co-condensation of polylysine conjugates with cationic lipids can lead to improvement in gene transfer efficiency. International Patent Application WO 95/02698 discloses the use of viral components to attempt to increase the efficiency of cationic lipid gene transfer.

Other methods of delivery of a vector according to the invention can be accomplished using nucleic acid condensing peptides. Nucleic acid condensing peptides, which are particularly useful for condensing the vector and delivering the vector to a cell, are described in WO 96/41606. Functional groups may be bound to peptides useful for delivery of a vector according to the invention, as described in WO 96/41606. These functional groups may include a ligand that targets a specific cell-type such as a monoclonal antibody, insulin, transferrin, asialoglycoprotein, or a sugar. The ligand thus may target cells in a non-specific manner or in a specific manner that is restricted with respect to cell type. Nucleic acid condensing agents useful in the invention include spermine, spermine derivatives, histones, cationic peptides, cationic non-peptides such as polyethyleneimine (PEI) and polylysine. Spermine derivatives refers to analogues and derivatives of spermine and include compounds as set forth in International Patent Application. WO 93/18759 (published Sep. 30, 1993). Delivery vehicles for delivery of DNA constructs to cells are known in the art and include DNA/polycation complexes which are specific for a cell surface receptor, as described in, for example, Wu and Wu, *J. Biol. Chem.* 263:14621 (1988); Wilson et al., *J. Biol. Chem.* 267:963 (1992); and U.S. Pat. No. 5,166,320).

In a preferred embodiment, the delivery vehicle comprises a functional group. The functional groups also may comprise a lipid, such as palmitoyl, oleyl, or stearoyl; a neutral hydrophilic polymer such as polyethylene glycol (PEG), or polyvinylpyrrolidine (PVP); a fusogenic peptide such as the HA peptide of influenza virus; or a recombinase or an integrase. The functional group also may comprise an intracellular trafficking protein such as a nuclear localisation sequence (NLS) and endosome escape signal or a signal directing a protein directly to the cytoplasm.

In a preferred embodiment, the stem cells are transformed with nucleic acids which encode for desired tissue specific targeting markers, such as for example, endothelial markers—VEGFR, Tie-1, EC-1, EnPo 1.

In another preferred embodiment, the invention provides methods for the targeting and tracking of stem cells to specific locations within an animal's body. The methods used herein are also useful in the therapeutic applications of repairing or colonizing specifically targeted areas within an animal, with stem cells, which then differentiate into mature cells of the specific cell type of the targeted area.

In a preferred embodiment, the method of the invention optionally comprises vectors expressing antibodies specific to antigens in a desired target area. A second antibody can be used for the in vivo tracking of the stem cell from any area in the animal's body to the desired target area.

In accordance with the invention, stem cells from a patient are harvested, sorted, purified and identified. The stem cells are then transduced with an expression vector comprising nucleic acid sequence encoding an antibody which will target the stem cell to the targeted location. In accordance with the invention, this procedure can be used for different antigen specificities of stem cells. Different isotypes of the arming antibody (e.g. IgG1, etc.) can be detected by utilizing secondary antibodies specific for the isotype. The secondary antibody can come from different sources, e.g. rat, sheep, goat etc; the important property being that it is targeted against the species of origin of the primary antibody. Also, secondary antibodies conjugated with different fluorochromes can be used, e.g. PE, FITC, APC, etc.

Alternatively, antibodies can be conjugated to a stem cells surface using linkers, chemical conjugates and the like.

In a preferred embodiment, exogenous DNA segments, for example, SCG 10; Na Channel II; glut-2, synapsin, epo, SCF, shh, wint, BMPs Ephrins, Pax-6, Emx-2, Mash-1, jagged 1 and 2, notch- and 2, ephrin B2 and ephrin B4, Bmi-1, Factor VIII, Factor IX, or mutant genes for β-glucocerebrosidase, erythropoietin ("EPO"), α-L-iduronidase, iduronate sulphatase, N-sulphatase, N-acetyl α-D-glucosaminidase, α-glucosamine-N-acetyltransferase, N-acetyl-α-D-glucosaminide-6-sulphatase, Galactosamine-6 sulphate sulphatase, β-galactosidase, N-acetyl-alactosamine-4-sulphatase, acid ceraminidase, acid sphingomyelinase, galactocerebroside β-galactosidase, arylsuphatase A, adenosine deaminase, α-L-fucosidase growth factors such as the interleukin family, angiogenesis stimulating or inhibiting factors such as the nitric oxide synthases (NOS1-3), vascular endothelial growth factors ("VEGF"), Angiostatin 1-7. Other examples of genes useful for introduction into isolated stem cells include those that encode Factor VIII, von Willebrand factor, insulin, tissue plasminogen activator, any of the interleukins, or a growth factor. Some examples of interleukins include IL-1, -2, -3, -4, -5, -6, -7, -8, -9, -10, -11, -12, -13, -14, -15, -16, -17, -18, -19, -20, and -21. Some examples of suitable growth factors include erythropoietin, thrombopoietin, PDGF, G-CSF, GM-CSF, IGF, TGFβ, VEGF, and BMP (bone morphogenic protein), different homeobox genes HOXB4, typically include an expression control DNA sequence operably linked to a tissue-specific promoter. Examples of tissue specific promoters are shown in Table 1. Below is a list of promoters additional to the tissue specific promoters listed above, cellular promoters/enhancers and inducible promoters/enhancers that could be; used in combination with the nucleic acid encoding a gene of interest in an expression construct. Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 1

PROMOTER AND/OR ENHANCER

Immunoglobulin Heavy Chain
Immunoglobulin Light Chain
T-Cell Receptor
HLA DQα and DQβ
β.-Interferon
Interleukin-2
Interleukin-2 Receptor
MHC Class II HLA-DRα
β-Actin
Muscle Creatine Kinase
Prealbumin (Transthyretin)
Elastase I
Metallothionein
Collagenase
Albumin Gene
α-Fetoprotein
τ-Globin
β-Globin
e-fos
c-HA-ras
Insulin
Neural Cell Adhesion Molecule (NCAM)
α1-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus

TABLE 2

| Element | Inducer |
| --- | --- |
| MT II | Phorbol Ester (TPA) |
|  | Heavy metals |
| MMTV (mouse mammary tumor virus) | Glucocorticoids |
| β-Interferon | poly(rI)X |
|  | poly(rc) |
| Adenovirus 5 E2 | E1A |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | E1A, SV40 Large T Antigen |
| Proliferin | Phorbol Ester-TPA |
| Tumor Necrosis Factor | FMA |
| Thyroid Stimulating Hormone Gene | α-Thyroid Hormone |
| Insulin E Box | Glucose |

The identity of tissue-specific promoters or elements, as well as assays to characterize their activity, is well known to those of skill in the art. Examples of such regions include the human LIMK2 gene (Nomoto et al. Gene, 236(2):259-271, 1999), the somatostatin receptor 2 gene (Kraus et al., FEBS Lett., 428(3):165-70, 1998), murine epididymal retinoic acid-binding gene (Lareyre et al., J. Bio. Chem., 274(12):8282-90, 1999), human CD4 (Zhao-Emonet et al., Biochim. Biophys. Acta, 1442(2-3):109-19, 1998), mouse alpha 2 (XI) collagen (Tsumaki, et al., 1998), D1A dopamine receptor gene (Lee, et al., DNA Cell Biol., 16(11):1267-75, 1997), insulin-like growth factor II (Wu et al., Biochem. Biophys. Res. Commun., 233(1):221-6, 1997; Wu et al., J. Med. Virol., 52:83-85. 1997), human platelet endothelial cell adhesion molecule-1 (Almendro et al., J Immunol., 157(12):5411-21, 1996).

Preferably, the expression control sequences will be eukaryotic promoter systems in vectors capable of transforming or transfecting stem host cells, but control sequences for prokaryotic hosts may also be used. Vectors can be constructed which also comprise a detectable/selectable marker gene. In preferred embodiments these marker genes are fluorescent proteins such as green fluorescent protein (GFP), cyan- (CFP), yellow- (YFG), blue- (BFP), red- (RFP) fluorescent proteins; enhanced green fluorescent protein (EGFP), EYFP, EBFP, Nile Red, dsRed, mutated, modified, or enhanced forms thereof, and the like.

As used herein, the "green-fluorescence protein" is a gene construct which in transfected or infected cells, respectively, shines green under ultraviolet light and thus enables the detection of a cell transfected or infected, respectively, with GFP in a simple manner. Uses of green fluorescent protein for the study of gene expression and protein localization are well known. The compact structure makes GFP very stable under diverse and/or harsh conditions such as protease treatment, making GFP an extremely useful reporter in general.

New versions of green fluorescent protein have been developed, such as a "humanized" GFP DNA, the protein product of which has increased synthesis in mammalian cells. One such humanized protein is "enhanced green fluorescent protein" (EGFP). Other mutations to green fluorescent protein have resulted in blue-, cyan- and yellow-green light emitting versions.

Endogenously fluorescent proteins have been isolated and cloned from a number of marine species including the sea pansies *Renilla reniformris, R. kollikeri* and *R. mullerei* and from the sea pens *Ptilosarcus, Stylatula* and *Acanthoptilum*, as well as from the Pacific Northwest jellyfish, *Aequorea victoria*; Szent-Gyorgyi et al. (SPIE conference 1999), D. C. Prasher et al., *Gene,* 111:229-233 (1992) and several species of coral (Matz et al. *Nature Biotechnology,* 17 969-973 (1999). These proteins are capable of forming a highly fluorescent, intrinsic chromophore through the cyclization and oxidation of internal amino acids within the protein that can be spectrally resolved from weakly fluorescent amino acids such as tryptophan and tyrosine.

In another preferred embodiment, stem cells comprise vectors expressing desired chemokines. Chemokines and cytokines play a powerful role in the development of an immune response. The role of chemokines in leukocyte trafficking is reviewed by Baggiolini (1998) *Nature* 392:565-8, in which it is suggested that migration responses in the complicated trafficking of lymphocytes of different types and degrees of activation will be mediated by chemokines. The use of small molecules to block chemokines is reviewed by Baggiolini and Moser (1997) *J. Exp. Med.* 186:1189-1191.

The role of various specific chemokines in lymphocyte homing has been previously described. For example, Campbell et al. (1998) *Science*, showed that SDF-1 (also called PBSF), 6-C-kine (also called Exodus-2), and MIP-3β (also called ELC or Exodus-3) induced adhesion of most circulating lymphocytes, including most CD4$^+$ T cells; and MIP-3α (also called LARC or Exodus-1) triggered adhesion of memory, but not naive, CD4$^+$ T cells. Tangemann et al. (1998) *J. Immunol.* 161:6330-7 disclose the role of secondary lymphoid-tissue chemokine (SLC), a high endothelial venule (HEV)-associated chemokine, with the homing of lymphocytes to secondary lymphoid organs. Campbell et al. (1998) *J. Cell Biol* 141(4):1053-9 describe the receptor for SLC as CCR7, and that its ligand, SLC, can trigger rapid integrin-dependent arrest of lymphocytes rolling under physiological shear.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination). Expression of proteins, may be controlled by any promoter/enhancer element known in the art, but these regulatory elements must be functional in the host selected for expression.

Expression vectors containing a nucleic acid encoding a desired polypeptide, can be detected or identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid a desired polypeptide is inserted within the "selection marker" gene sequence of the vector, recombinants containing the protein insert can be identified by the absence of the gene function.

Stem Cell Maturity and Cell Differentiation

In accordance with the invention, it is desirable to determine cell maturity and differentiation. Several different ways, to assess maturity and cell differentiation, are available. For example, one such method is by measuring cell phenotypes. The phenotypic changes can be evaluated by flow cytometry after immunofluorescent staining using monoclonal antibodies that will bind membrane proteins characteristic of various cell types.

Introducing Cells into the Biocompatible Material

If desired, cells can be introduced into a porous biocompatible material. Generally, cells are introduced into the material of the present invention in vitro, although in vivo seeding approaches are employed in some circumstances. It is important that adequate growth (or storage) medium be provided to ensure cell viability. If the composition is to be implanted for use in vivo after in vitro seeding, sufficient growth medium must be supplied to ensure viability throughout, and for a short time following, the implant proceeding. Once the composition has been implanted, the porous nature of the material allows the cells' nutritional requirements to be met by the circulating fluids of the host.

Dulbecco's minimal essential medium to be particularly useful in the practice of the present invention. Other solutions that may be employed include, but are not limited to, phosphate-buffered saline; carbonate-, HEPES-, or TRIS-buffered solutions. In some cases, additional growth-stimulating components, such as serum, growth factors, amino acid nutrients, sugars, and salts, may be added to the aqueous solution employed in the present invention.

In the embodiment, wherein the biocompatible material is porous, cells are able to readily migrate into it. Any available method may be employed to introduce the cells to the material. For example, cells may be introduced by means such as culturing, pressure, vacuum, or osmosis. Alternatively (or additionally), cells may be layered on the material, or the material may be dipped into a cell suspension and allowed to remain there under conditions and for a time sufficient for cells to impregnate the material. Generally, it is desirable to avoid excessive manual manipulation of the cells in order to minimize cell death during the impregnation procedure. Cells may also be introduced into the material in vivo simply by placing the material in the body adjacent a source of desired cells. In some cases, it may be desirable to enhance such in vivo cell impregnation by including within the material an appropriate chemotactic factor, associative factor (i.e., a factor to which cells bind), or factor that induces differentiation of cells into the desired cell type.

As those of ordinary skill will readily appreciate, the number of cells to be introduced into the inventive material will vary based on the intended application of the seeded material and on the type of cell used. Where dividing autologous cells are being introduced by use of 5,000-1,000,000 cells per cm$^3$ are expected to result in cellular proliferation and extracellular matrix formation within the material. Where non-dividing cells are employed, larger numbers of cells will generally be required. In those cases where seeding is accomplished by host cell migration into the material in vivo, exposure of the material to fluids containing cells (e.g., bone-forming cells), or to tissue (e.g., bone) itself is effective to seed the material with cells without the need for inoculation with a specified number of cells.

Applications

Mammalian bone tissue has a remarkable ability to regenerate and thereby repair injuries and other defects. For example, bone growth is generally sufficient to bring about full recovery from most simple and hairline fractures. Unfortunately, however, there are many injuries, defects or conditions where bone growth is inadequate to achieve an acceptable outcome. For example bone regeneration generally does not occur throughout large voids or spaces. Therefore, fractures cannot heal unless the pieces are in close proximity. If a significant amount of bone tissue was lost as a result of the injury, the healing process may be incomplete, resulting in undesirable cosmetic and/or mechanical outcomes. This is often the case with non-union fractures or with bone injuries resulting from massive trauma. Tissue growth is also generally inadequate in voids and segmental gaps in bone caused, for example, by surgical removal of tumors or cysts. In other instances, it may be desirable to stimulate bone growth where bone is not normally found, i.e., ectopically. Spine fusion to relieve lower back pain where two or more vertebrae are induced to fuse is one example of desirable ectopic bone formation. Currently, such gaps or segmental defects require bone grafts for successful repair or gap filling. The development of effective bone graft substitutes would eliminate the need to harvest bone from a second surgical site for a graft procedure, thereby significantly reducing the discomfort experienced by the patient and risk of donor site healing complications.

The combination of stem cells and the biocompatible material, referred to herein as "the composition" or "biocomposition", can be usefully employed in any of a variety of in vivo and in vitro systems. For example, the material may be used in bone tissue or repair applications or augmentation plastic therapy in vivo. Alternatively or additionally, the material may be employed as a stem cell adhesion membrane or matrix. The material may also be utilized in artificial organ construction or repair.

In vitro, the material may be used as a three dimensional cell culture matrix, and as a model for analyzing osteoclast, osteoblast, chondrocyte, and/or macrophage cultures, progenitor cell differentiation, and/or reossification and calcium phosphate resorption. The material is particularly useful for tissue formation and/or degradation studies, for example employing cells such as progenitor cells, stem cells, osteocytes, osteoclasts, osteoblasts, chondrocytes, macrophages, myoblasts, and fibroblasts. Certain preferred applications are discussed in more detail below, but the discussion is intended only for purposes of exemplification and is not intended to be limiting.

Bone Production and Healing: In preferred embodiments of the present invention, the biocompatible material is cultured with bone-forming cells or precursors thereof. Preferably, the biocompatible material is formulated, and the cell population is selected, so that the biocompatible material becomes ossified within a period of about 4-12 weeks.

In particularly preferred embodiments of the invention, the culturing is accomplished by placing the biocompatible material in contact with a source of the host's own bone-producing cells. Such cells are found in bone tissue or in bone-associated blood or fluids, including exogenous fluids that have been in contact with bone (including cancerous bone), bone materials, or bone regions such as the periosteum or the marrow.

In a preferred embodiment, the stem cells are autologous stem cells. Bone forming cells harvested from the host are cultured in vitro so that the composition is implanted in the host with the stem cells attached to the surface of the biocompatible material. Furthermore, culturing of non-autologous stem cells is also within the scope of the invention. Such non-autologous cells can be obtained from any of a variety of sources, including but not limited to primary sources, cell lines, and cell banks.

Bone formation in and around the composition can be enhanced by the incorporation of trophic factors and/or bone-growth inducing factors into, or onto, the biocompatible material device.

Osseous Augmentation: The compositions of the present invention are useful for the enhancement or alteration of the shape of bony structures (e.g., a chin). For such applications, the composition may be supplied in a desired shape and applied to a bony surface. The compositions employed in augmentation applications maybe seeded, if desired through application of cells or cell lines to the biocompatible material, although some preferred embodiments involve host cell seeding. The term "host cell seeding" encompasses any method by which cells of the host are introduced into the biocompatible material. For example, the term encompasses migration of host cells into a device implanted in vivo, as well as assisted migration accomplished by placing bone blood or fragments of the periosteum on or in contact with the device (in vivo or in vitro), among other things.

Cartilage Production and Healing: Damage to cartilage can result in serious physical deformations. Currently, the most common treatment for loss of cartilage is replacement with a prosthetic material, but many difficulties have been encountered with this approach. The compositions of the present invention offer an attractive alternative in which the biocompatible material acts as a formable scaffold into and within which tissue can grow.

The biocompatible material of the present invention can be porous so it can be seeded with stem cells as well as attachment of stem cells on the surface of the biocompatible material. Preferably, the cells are cultured as described in detail in the examples which follow, by placing the device in contact with a source of the host's own cartilage-forming cells (e.g., chondrocytes) or precursors thereto. Such cells are found in cartilage-associated blood or fluids, including exogenous fluids that have been in contact with cartilage or cartilagenous materials. Thus, fluids that have been in contact with the perichondrium, cartilage, or marrow typically contain such cells.

In many cases, e.g., a biocomposition designed for augmentation of a damaged ear, seeding can be accomplished by placing the biocomposition in contact with the breached region of the perichondrium. In other cases, it will be useful to surgically prepare a seating for the biocomposition within existing cartilaginous tissue by removing a portion of the cartilage at the implant site.

In some embodiments of the present invention, additional steps may be taken to augment chondrogenesis associated with the cells and biocompatible material. For example, cartilage-forming cells harvested from the patient may be introduced into the device in addition (or as an alternative to) cells that impregnate it after implantation in vivo. Alternatively or additionally, trophic factors or cartilage growth-inducing factors may be incorporated into or onto the device.

It should be clear that autologous cells are not required for the biocomposition employed in cartilage-forming applications; non-autologous cells are also within the scope of the invention so long as the cells are selected and the biocompatible material is formulated so that a desired amount of cartilage regeneration occurs prior to host rejection of the cartilage-forming cells. Thus, cells or tissues obtained from primary sources, cells lines, or cell banks are useful in the practice of this embodiment of the present invention.

Ectopic Bone or Cartilage Production: The biocompositions of the present invention can be used to produce bone or cartilage formation at a site at which bone or cartilage does not normally occur. Introduction of a biocomposition into which bone- or cartilage-producing cells have been seeded into an in vivo implant site will result in bone or cartilage formation at that site. In preferred embodiments, the biocomposition contains growth and/or trophic factors in addition to the cells, so that maintenance of the ectopically-formed bone or cartilage can be prolonged. Once it has been produced, such ectopic tissue may either be left in place or may be surgically removed, depending on its intended use. Alternatively or additionally, trophic or growth factors external to the implant may be provided, e.g., through the use of encapsulated cells, polymer implants, or other method of factor delivery (see, for example, Aebischer et al., U.S. Pat. No. 4,892, 538; Sefton, U.S. Pat. No. 4,353,888 and Winn et al. Experimental Neurology 140:126 (1996)).

Research Applications: The biocompositions of the present invention, due to its ease of preparation, mild formation conditions, sparing solubility in most aqueous systems, and tractability, provides an attractive three-dimensional growth matrix for use in research and production tissue culture applications. Furthermore, the material is useful for tissue formation and/or degradation studies (e.g., of bone or cartilage). Preferably, the material employed in such studies comprises cells attached to the surface, and/or is porous to allow seeding with cells. Examples of cells include (but not limited to) progenitor cells, stem cells, osteocytes, osteoclasts, osteoblasts, chondrocytes, macrophages, myoblasts, and fibroblasts.

Diagnostics: The biocompositions of the present invention may be employed in diagnostics that detect various health or disease states. For example, the biocomposition can be used in qualitative or quantitative assays to determine the bone- or cartilage-forming potential of cells taken from a patient to be diagnosed. The biocomposition can also be used in diagnostics to assay vascularization and hard tissue degradation. Various soft tissue diagnostics are also made possible with the biocompositions.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

It should be understood that the Examples described below are provided for illustrative purposes only and do not in any way define the scope of the invention.

Example 1

Stem Cell Adhesion

Simulated bone made of ceria stabilized zirconia was sterilized via dry cycle autoclave and co-cultured with human progenitor cells or stem cells in DMEM culture media supplemented with 10% bovine fetal serum for 24 hours. The porous prototype article was made by near-net shape plasma nanomanufacturing as described above. The human progenitor cells were cultured in a T75 tissue culture flask using media consisting of DMEM Gibco (Dulbeccos modified eagles medium). 10% FBS Novacell (Fetal Bovine Serum). 1% Antibiotic/Antimycotic Gibco till they reach approximately 80% confluency. The medium was decanted from flask into waste container and 5 ml of trypsin (0.25% Gibco/Invitrogen) was added to flask. The flask was incubated for 90 seconds @ 37° C. and 10 ml of plain DMEM was added ip deactivate trypsin. Contents of flask (cell suspension) was decanted into a 50 ml conical tube. The cell suspension was centrifuged for 5 min @ 300 RPM, supernatant was removed from 50 ml conical tube. The cell suspension was then plated into 6 well tissue culture plates at approximately 25,000 per well.

The cells on the material surface were visualized using staining with green fluorescent dye. For the transfection of green fluorescent protein vector, a reposomal-transfection method was used. For staining with the dye, cells were incubated in media containing 30 μM of the dye for few hours.

The NT2/D1 cells were seeded ($5 \times 10^6$ cells per 150 mm petri dish) in Dulbecco's modified Eagle's medium with F-12 (DMEM/F-12; Invitrogen) supplemented with 10% heat inactivated fetal bovine serum (Novacell), 1% antibiotic-antimycotic (Invitrogen), 4 mM glutamine (Invitrogen) and maintained in a humidified atmosphere of 5% $CO_2$/95% air at 37° C.). The cells were passed twice a week by short exposure to trypsin/EDTA (Invitrogen). For the experiments, $1 \times 10$ NT-2/D1 cells were plated on the synthetic bone in a 6 well tissue culture plate. EGFP expression or green fluorescent dye in the cells was detected as green fluorescence signals under a microscope (Leica, model DMRB).

FIG. 1 shows a scanned image of mesenchymal stem cells isolated from adult human bone marrow stained with green fluorescent dye. The green stained cells 120 can be seen to be in various size areas bound to the darker synthetic bone 110. The stained cells 120 appear as light regions 120 in the black and white figure provided.

Since mesenchymal stem cells are committed to produces bone and other connecting tissue, it is expected to accelerate healing process of the bone. However, mesenchymal stem cells are well known to not bind to most materials, including de-calcified real bone. Thus, the binding of the cells to the synthetic bone is itself highly significant. Since the bone material is bio-compatible, the mesenchymal stem cells will provide a bridge between the endogenous tissue (bone) and the synthetic bone.

Example 2

Biomedical Application

Figure 2:
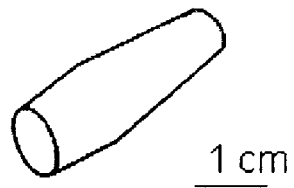
FIG. 2 shows a scanned image of a porous, near-net shape ceria-stabilized zirconia article for a specific bio-medical application formed using a plasma spraying process according to the invention.

A porous, near-net shape ceria-stabilized zirconia article for a specific biomedical application was formed using a plasma spraying process. A scanned image of the article is shown in FIG. 2. The cylindrical shape and size were specifically designed for this application, simulating the shape and size of a bone segment. Thus, the plasma processing is an effective method for consolidation of nanomaterials to large near-net-shape components with the desired shape and size. The experimental parameters for developing of the Ceria-stabilized Zirconia component were selected as following: current: 850 Amps, primary Gas: Ar: 82 SCFH, secondary gas: He: 40 SCFH, powder feeding rate: 2.5 RPM, carrier gas: 13 SCFH.

It was found that when there is an increase of the ceria concentration in the Ceria stabilized Zirconia system, the amount of the tetragonal phase increases and the grain size of Zirconia decreases. An 18% Ceria content powder was used for plasma developing of the desired component.

The developed material was characterized with modern equipment. Using X-Ray Diffraction (XRD), it was clear that there is some amount of monoclinic phase in the Ceria stabilized Zirconia powder. Previously, it had been found that the Zirconia femoral heads undergo surface degradation and reduction of mechanical properties as result of the tetragonal (t) to monoclinic (in) phase transformation. Thus the dilatation and shear strains associated with the t→transformation can be the reason for microcracking and degradation of the material. However, in this experiment, after the plasma processing the only phase detected was a non-equilibrium tetragonal t' phase. As a result, the existence of this metastable tetragonal phase in the plasma-sprayed $CeO_2$ stabilized $ZrO_2$ may be beneficial to the biological tissue growth in this experiment.

From the X-Ray Photoelectron Spectroscopy (XPS) characterization of the as-sprayed near-net shape part it was found that the $Ce^{+4}$ concentrations on the surface of the component are higher than in the powder before spraying. The $C^{+4}$ oxidation state transformation can be attributed to some degree of oxidation during part manufacturing. In this case, however, the $Ce^{+3}$ states are still present, which can be a key promoter for the bio-cell compatibility. The developed advanced scaffolds show comparable bioactivity for the first time and improved bonding strength to the biological tissues—possibly due to the $Ce^{+3}$ states.

Therefore, this preferred embodiment of the invention combines the benefits of the plasma nano-manufacturing to near-net-shape components with various shapes. In addition, the benefits of both Cerium Oxide and its unique oxidation state transformations and the non-equilibrium tetragonal phase formation as result of the plasma processing are incorporated. All K combined, these benefits lead to better properties and enhanced bio-medical functions of the material.

Other Embodiments

It is to be understood that while the invention has been described in conjunction with the detailed description thereof, the foregoing description is intended to illustrate and not limit the scope of the invention.

All references cited herein, are incorporated herein by reference.

We claim:

1. A biocomposite, comprising:
   a biocompatible solid material, and
   a plurality of living human progenitor or living stem cells attached to a surface of said biocompatible material;
   wherein the biocompatible material comprises cerium nanoparticles on surfaces of said biocompatible material;
   wherein the cerium nanoparticles comprise ceria nanoparticles having $Ce^{4+}$ molecules and reduced ceria nanoparticles having $Ce^{3+}$ molecules, the cerium nanoparticles having an average particle size of less than 20 nm; and
   wherein the average particle size of less than 20 nm is effective to provide an increased amount of the reduced ceria nanoparticles on the surfaces of said biocompatible material relative to larger cerium nanoparticles.

2. The biocomposite of claim 1, wherein said biocompatible material is a porous material.

3. The biocomposite of claim 1, wherein said biocompatible material comprises ceria stabilized zirconia.

4. The biocomposite of claim 1, wherein the surface of the biocompatible material comprises about 10% to about 90% $Ce^{3+}$ molecules versus $Ce^{4+}$ molecules.

5. The biocomposite of claim 1, wherein the surface of the biocompatible material comprises at least 10% $Ce^{3+}$ molecules versus $Ce^{4+}$ molecules.

6. The biocomposite of claim 1, wherein the surface of the biocompatible material comprises about 20% $Ce^{3+}$ molecules versus $Ce^{4+}$ molecules.

7. The biocomposite of claim 1, wherein the surface of the biocompatible material comprises about 30% $Ce^{3+}$ molecules versus $Ce^{4+}$ molecules.

8. The biocomposite of claim 1, wherein the surface of the biocompatible material comprises about 10% to about 99% $Ce^{4+}$ molecules versus $Ce^{3+}$ molecules.

9. The biocomposite of claim 1, wherein the stem cells are derived from autologous bone marrow.

10. The biocomposite of claim 1 wherein the stem cells are selected from $Lin^-$, $Sca-1^+$, or $c-kit^+$.

11. The biocomposite of claim 1, wherein said biocompatible material comprises a porous, near-net shape macroscopic article formed using a plasma spraying process.

12. The biocomposite of claim 1, wherein said biocompatible material further comprises a coating of cell-adhesion molecules.

13. The biocomposite of claim 1, wherein said plurality of living human progenitor or living stem cells have been contacted with a gene encoding a bone morphogenic protein.

14. The biocomposite of claim 1, wherein the cerium nanoparticles are in a non-agglomerated state.

* * * * *